(12) United States Patent
Barber et al.

(10) Patent No.: US 8,940,484 B2
(45) Date of Patent: *Jan. 27, 2015

(54) FORENSIC IDENTIFICATION

(71) Applicant: QIAGEN GmbH, Hilden (DE)

(72) Inventors: Rebecca A. L. Barber, Hilden (DE);
Michael D. Barber, Hilden (DE); Peter E. Johnson, Hilden (DE); Sharon M. Gillbard, Hilden (DE); Marc D. Haywood, Hilden (DE); Carolyn D. Smith, Hilden (DE); Jennifer A. Arnold, Hilden (DE); Trudy Burke, Hilden (DE); Andrew J. Urquhart, Hilden (DE); Peter P. Gill, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,648

(22) Filed: Feb. 7, 2013

(65) Prior Publication Data

US 2013/0144047 A1 Jun. 6, 2013

Related U.S. Application Data

(63) Continuation of application No. 13/330,581, filed on Dec. 19, 2011, now Pat. No. 8,399,191, which is a continuation of application No. 13/089,099, filed on Apr. 18, 2011, now abandoned, which is a continuation of application No. 12/632,608, filed on Dec. 7, 2009, now abandoned, which is a continuation of application No. 11/821,259, filed on Jun. 21, 2007, now Pat. No. 7,645,580, which is a continuation of application No. 11/244,331, filed on Oct. 4, 2005, now abandoned, which is a continuation of application No. 09/910,183, filed on Jul. 20, 2001, now Pat. No. 7,087,380, which is a continuation of application No. 09/706,525, filed on Nov. 3, 2000, now abandoned, which is a continuation of application No. 09/498,567, filed on Feb. 4, 2000, now abandoned, which is a continuation of application No. 09/107,029, filed on Jun. 29, 1998, now abandoned.

(30) Foreign Application Priority Data

Jun. 28, 1997 (GB) .................................. 9713597.4

(51) Int. Cl.
*C12Q 1/68* (2006.01)
*C07H 21/00* (2006.01)
*C07H 21/02* (2006.01)
*C07H 21/04* (2006.01)

(52) U.S. Cl.
CPC .............. *C07H 21/04* (2013.01); *C12Q 1/6827* (2013.01); *C12Q 1/6876* (2013.01); *C12Q 1/6881* (2013.01); *C12Q 1/6888* (2013.01); *C12Q 2600/156* (2013.01); *C12Q 2600/172* (2013.01)
USPC .......... 435/6.1; 536/22.1; 536/23.1; 536/24.3

(58) Field of Classification Search
USPC ....................... 435/6.1; 536/22.1, 23.1, 24.3
See application file for complete search history.

(56) References Cited

U.S. PATENT DOCUMENTS

| | | | |
|---|---|---|---|
| 5,364,759 A | 11/1994 | Caskey et al. | |
| 5,599,666 A | 2/1997 | Schumm et al. | |
| 5,688,642 A * | 11/1997 | Chrisey et al. | 435/6.11 |
| 6,156,512 A | 12/2000 | Schumm et al. | |
| RE37,984 E | 2/2003 | Jackie et al. | |
| 7,008,771 B1 | 3/2006 | Schumm et al. | |
| 7,087,380 B2 * | 8/2006 | Griffiths et al. | 435/6.11 |
| 7,645,580 B2 * | 1/2010 | Barber et al. | 435/6.11 |
| 8,399,191 B2 * | 3/2013 | Barber et al. | 435/6.1 |

OTHER PUBLICATIONS

Gulati et al., Conditions for Using DNA Polymerase I as an RNA-Dependent DNA Polymerase. PNAS 71(4) :1035 (1974).*
Lichter et al. Rapid detection of human chromosome 21 aberrations by in situ hybridization. PNAS 85 :9664 (1988).*
Barber et al. [International J. of Legal Medicine [109 : 62 (1996)].*
Smith and Waterman Identification of common molecular subsequences. Journal of Molecular Biology 147 : 195 (1981).*
Pearson et al., Improved tools for biological sequence comparison. PNAS 85 : 2444 (1988).*
Mannucci, et al., "Forensic application of a rapid and quantitative DNA sex test by amplification of the X-Y homologous gene amelogenin", International J. of Legal Medicine, 106:190(1994).
A. Moller, et al., *Different types of structural variation in STRs: HumFES/FPS, HumVWA and HumD21S11*, International Journal of Legal Medicine, vol. 106, 1994, pp. 319-323.
Christoph Peurs et al., *Identification of Repeat Sequence Heterogeneity at the Polymorphic Short Tandem Repeat Locus HUMTH01[AATG]$_n$ and Reassignment of Alleles in Population Analysis by Using a Locus-specific Allelic Ladder*, American Journal of Human Genetics, 53, 1993, pp. 953-958.
Colin Kimpton et al., *Report on the second EDNAP collaborative STR exercise*, Forensic Science International, vol. 71, 1995, pp. 137-152.
Florence Rousselet et al., *A Pentaples Automated Fluorescent Typing system for Forensic Identification and French Caucasian Population Data*, Journal of Forensic Sciences, vol. 42, No. 3, May 1997, pp. 500-503.
R.A.L. Griffiths, et al., *New reference allelic Ladders to improve allelic designation in a multiplex STR system*, International Journal of Legal Medicine, vol. 111, 1998. pp. 267-272.
D.J. Mancuso, et al., *Human von Willebrnad Factor Gene, Exon 39, 40, 31, and 42 and Alu repetitive element*, NCBI; Jan. 14, 1995, retreived from http://www.ncbi.nlm.nih.gov, database accession No. M25858, XP002213448.

(Continued)

*Primary Examiner* — Ethan Whisenant
(74) *Attorney, Agent, or Firm* — Panelli Haag & Kilger PLLC

(57) ABSTRACT

The invention provides allelic ladder mixtures and individual alleles suitable for use in such mixtures. The allelic ladder mixtures give improved identification and distinguishing capabilities, particularly suitable in forensic investigations.

1 Claim, 7 Drawing Sheets

(56) References Cited

OTHER PUBLICATIONS

P. Gill, et al., A new method of STR interpretation using inferential logic—development of a criminal intelligence database, International Journal of Legal Medicine, vol. 109, 1996, pp. 14-22.

Barber et al., Sequence analysis and allelic designation of the two short tandem repeat loci D18S51 and D8S1179, Intl. J. of Legal Medicine, 109:62-65 (1996).

Bodowie et al., Analysis of the VNTR locus D1S80 by the PCR followed by high-resolution page, Am. J. of Human Genetics, 48:137-144 (1991).

Edwards et al., DNA typing and genetic-mapping with trimeric and tetrameric tandem repeats, Am. J. of Human Genetics, 49:746-756 (1991).

Kimpton et al., Validation of highly discriminating multiplex short tandem repeat amplification systems for individual identification, Electrophoresis, 17:1283-1293 (1996).

Sharma et al., Tetranucleolide repeat polymorphism at the D21S11 locus, Human Mol. Genet., 1(1):67 (1992).

Sullivan et al., A rapid and quantitive DNA sex test: fluorescence-based PCR analysis of X-Y homologous gene amelogenin, BioTechniques, 15(4):636-641 (1993).

M.D. Barber et al., Structural Variation in the Alleles of a Short Tandem Repeat System at the Human Alpha Fibrinogen Locus, International Journal of Legal Medicine, vol. 108, 1996, pp. 180-185.

Peter Gill et al., Considerations from the European DNA Profiling Group (EDNAP) Concerning STR Nomenclature, Forensic Science International, vol. 87, 1997, pp. 185-192.

H-g. Zhou et al., The HumD21S11 System of Short Tandem Repeat DNA Polymorphisms in Japanese and Chinese, forensic Science International, vol. 86, 1997, pp. 109-118.

B. Brinkmann et al, Complex Mutational Events at the HumD21S11 Locus, Human Genetics, vol. 98, 1996, pp. 60-64.

Cecelia A. Crouse et al., Investigation of Species Specificity Using Nine PCR-Based Human STR Systems, Journal of Forensic Science, vol. 40, No. 6, Nov. 1995, pp. 952-956.

R. Sparkes et al., The Validation of a 7-locus Multiplex STR Test for Use in Forensic Casework, International Journal of Legal Medicine, vol. 109, 1996, pp. 195-204.

M.D. Barber, et al., Structural Variation of Novel Alleles at the Hum vWA and Hum FES/FPS Short Tandem Repeat Loci, International Journal of Medicine, vol. 108, 1995, pp. 31-35.

F. Rousselet et al., French Caucasian Population Data Obtained from Fluorescently Detected HumvWFA31/A and HumF13A01 Short Tandem Repeat Loci, International Journal of Medicine, vol. 109, 1996, pp. 5-9.

M. D. Barber et al., Sequence Analysis and Allelic Designation of the Two Short Tandem Repeat Loci D18S51 and D8S1179, Int. J. Legal Med., vol. 109, 1996, pp. 62-65.

D. J. Mancuso et al., Structure of the Gene for Human Von Willebrand Factor, J. Biol. Chem., vol. 264, No. 33, 1989, revised Jul. 5, 2002, Database Genebank, NCBI.

Bruce Budowle et al., Analysis of the VNTR Locus D1S80 by the PCR Followed by High-Resolution PAGE, Am. J. Hum. Genet., vol. 48, 1991, pp. 137-144.

Al Edwards et al., DNA Typing and Genetic Mapping with Trimeric and Tetrameric Tandem Repeats, Am. J. Hum. Gent., vol. 49, 1991, pp. 746-756.

Colin P. Kimpton et al., Validation of Highly Discriminating Multiplex Short Tandem Repeat Amplification Systems for Individual Identification, Electrophoresis, vol. 17, 1996, pp. 1283-1293.

V. Sharma et al., Tetranucleotide Repeat Polymorphism at the D21S11 Locus, Human Moelcular Genetics, vol. 1, No. 1, 1992, p. 67.

Kevin M. Sullivan et al., A Rapid and Quantitative DNA Set Test: Fluorescence-Based PCR Analysis of X-Y Homologous Gene Amelogenin, BioTechniques, vol. 15, No. 4, 1993, pp. 636-641.

B. Brinkmann, Population Genetic Comparisons Among Eight Populations Using Allele Frequency and Sequence Data From Three Microsatellite Loci, Eur. J. Hum. Genet., vol. 4, 1996, pp. 175-182.

Cynthia J. Sprecher et al., General Approach to Analysis of Polymorphic short Tandem Repeat Loci, BioTechniques, vol. 20, No. 2, Feb. 1996, pp. 266-276.

B.M. Dupuy et al., A dedicated Internal Standard in Fragment Length Analysis of Hyperpolymorphic short Tandem Repeats, Forensic Science International, vol. 85, 1997, pp. 207-227.

Editorial, DNA Recommendations—Further Report of DNA Commission of the ISFH Regarding the Use of Short Tandem Repeat Systems, Forensic Science International, vol. 87, 1997, pp. 179-184.

Peter Gill et al., Report of the European DNA Profiling Group (EDNAP): An Investigation of the Complex STR Loci D21S11 and JUMFIBRA (FGA), Forensic Science International, vol. 86, 1997, pp. 25-33.

C. Kimpton et al., A Further Tetranucleotide Repeat Polymorphism in the vWF Gene, Human Molecular Genetics, vol. 1, No. 4, 1992, pp. 287.

M. Klintschar et al., A Study of the Short Tandem Repeat Systems, HUMVWA and HUMTH01 in an Austrian Population Sample, Int. J. Legal. Med., vol. 107, 1995, pp. 329-330.

Andy Urquhart et al., Highly Discrimmating Heptaplex short Tandem Repeat PCR System for Forensic Identification, BioTechniques, vol. 18, No. 1, 1995, pp. 116-121.

Peter Gill et al., Automated Short Tandem Repeat (STR) Analysis in Forensic Casework—A Strategy for the Future, Electrophoresis, vol. 16, 1995, pp. 1543-1552.

Nicola J. Oldroyd et al., A Highly Discriminating Octoplex Short Tandem Repeat Polymerase Chain Reaction System Suitable for Human Individual Identification, Electrophoresis, vol. 16, 1995, pp. 334-337.

Kathleen A. Mills et al., Tetranucleotide Repeat Polymorphism at the Human Alpha Fibrinogen Locus (FGA), Human Molecular Genetics, vol. 1, No. 9, Dec. 1992, pp. 779.

X. Tang et al., Generation of Nineteen STS Markers that can be Anchored at Specific Sites on Human Chromosome 21, unpublished, 1992, Genebank Accession No. M95976.

X. Tang et al., Generation of Nineteen STS Markers that can be Anchored at Specific Sites on Human Chromosome 21, unpublished, 1992, Genebank Accession No. M95977.

Chantal J. Fregeau et al., DNA Typing with Fluorescently Tagged Short Tandem Repeats A Sensitive and Accurate Approach to Human Identification, BioTechniques, vol. 15, No. 1, 1993, pp. 100-119.

S.C. Gerken et al., Genetic and Physical Mapping of Simple Sequence Repeat Containing Sequence Tagged Sites from the Human Genome, unpublished, 1993, Genebank Accession No. L18333.

D.W. Chung et al., Nucleotide Sequences of the Three Genes Coding for Human Fibrinogen, Fibrinogen, Thrombosis, Coagulation and Fibrinolysis, Plenum Press, New York, 1991, pp. 39-48. Genebank Accession No. M64982.

M. D. Barber et al., Structural Variation in the Alleles of a Short Tandem Repeat System at the Human Alpha Fibrinogen Locus, Int. J. Legal Med., vol. 108, 1996, pp. 180-185.

P. Gill et al., Report of the European DNA Profiling Group (EDNAP)—Towards Standardisation of Short Tandem Repeat (STR) Loci, Forensic Science International, vol. 65, 1994, pp. 51-59.

Colin Kimpton et al., Evaluation of an Automated DNA Profiling System Employing Multiplex Amplification of Four Tetrameric STR Loci, Int. J. Leg. Med., vol. 106, 1994, pp. 302-311.

A. Urquhart et al., Variation in Short Tandem Repeat Sequences—A Survey of Twelve Microsatellite Loci for Use as Forensic Identification Markers, Int. J. Leg. Med, vol. 107, 1994, pp. 13-20.

J. E. Lygo et al., The Validation of Short Tandem Repeat (STR) Loci for Use in Forensic Casework, Int. J. Leg. Med, vol. 107, 1994, pp. 78-89.

Antti Sajantila et al., A Microsatellite Polymorphism in the von Willebrand Factor Gene: Comparison of Allele Frequencies in Different Population Samples and Evalutaion for Forensic Medicine, Forensic Science International, vol. 68, 1994, pp. 91-102.

Stig Holgersson et al., Fluorescent-based Typing of the Two Short Tandem Repeat Loci HUMTH01 and HUMACTBP2: Reproducibility of Size Measurements and Genetic Variation in the Swedish Population, Electrophoresis, vol. 15, 1994, pp. 890-895.

(56) References Cited

OTHER PUBLICATIONS

B. Brinkmann et al., Structure of New Mutations in 2 STR Systems, Int. J. Leg. Med. vol. 107, 1995, pp. 201-203.
P. Berschick et al., Analysis of the Short Tandem Repeat Polymorphism D18S51: Allele Frequencies and Sequence Studies, unpublished, 1995, Genebank Accession No. X91255.
P. Berschick et al., Analysis of the Short Tandem Repeat Polymorphism D18S51: Allele Frequencies and Sequence Studies, unpublished, 1995, Genebank Accession No. X91254.
P. Berschick et al., Analysis of the Short Tandem Repeat Polymorphism D18S51: Allele Frequencies and Sequence Studies, unpublished, 1995, Genebank Accession No. X91253.
J. Murray et al., Cooperative Human Linkage Center, unpublished, 1995, Genebank Accession No. G08710.
D.J. Mancuso et al., Structure of the Gene for Human von Willebrand Factor, J. Biol. Chem., vol. 264, No. 33, pp. 19514-19527, Genebank Accession No. M25858.
Atsushi Nagai et al., Analysis of the STR Loci HUMF13A01, HUMFX111B, HUMLIPOL, HUMTH01, HUMTPOX and HUMVWFA31 in a Japanese Population, Int. J. Leg. Med, vol. 109, 1996, pp. 34-36.
Ann M. Lins et al., Multiplex Sets for the Amplification of Polymorphic Short Tandem Repeat Loci—Silver Stain and Fluorescence Detection, BioTechniques, vol. 20, No. 5, 1996, pp. 882-889.
Ronny Decorte et al., Evaluation of the ALF DNA Sequencer for High-speed Sizing of Short Tandem Repeat Alleles, Electrophoresis, vol. 17, 1996, pp. 1542-1549.
Jian Tie et al., Analysis of STR Polymorphisms Using Capillary Gel Electrophoresis, Res. Pract. Forens. Med., vol. 39, 1996, pp. 15-19, partial English translation.
I. W. Evett et al., Statistical Analysis of Data for Three British Ethnic Groups from a New STR Multiplex, Int. J. Leg. Med, vol. 110, 1997, pp. 5-9.
B. Rolf et al., Automatische Analyse von Hoch Effizienten STRs, Rechtsmedizin, vol. 7, 1997, pp. 157-161.
David E. O. Van Hoffstat et al., Population Genetic Study of Four Short Tandem Repeat Loci in the Belgian Population, Using Capillary Electrophoresis, Electrophoresis, vol. 19, 1998, pp. 719-722.
Peng-Xia Xiao et al., Quadruplex Fluorescent STR Typing System (HUMVWA, HUMTH01, D21S11 and HPTR) with Sequence-defined Allelic Ladders Identification of a New Allele at D21S11, Forensic Science International, vol. 94, 1998, pp. 39-46.
E. Mornhinweg et al., D3S1358 and D8S1179: Analysis and Allele Frequencies in a South German Population, Progress in Forensic Genetics 7, Proceedings of the 17th International ISFH Congress, Oslo, Sep. 1997, pp. 315-316.
Danula Miscicka-Sliwka et al., A Study of Sequence Polymorphism in Human Alpha Fibrinogen Gene in the Pomerania-Kujawy Region of Poland. Identification of a New Allele and Two Alleles Previously Reported to be Absent in Caucasians, Progress in Forensic Genetics 7, Proceedings of the 17th International ISFH Congress, Oslo, Sep. 1997, pp. 384-386.
DNA Polymorphism, Chapter 3, D12S76 D21S11 Locus, vol. 6, Dec. 1997, no English translation.
DNA Polymorphism, Chapter 5, PCT-SSCP TH01, vol. 6, Dec. 1997, no English translation.
Office Action submitted in U.S. Appl. No. 09/107,029, dated Jun. 24, 1999.
Office Action submitted in U.S. Appl. No. 09/107,029, dated Aug. 4, 1999.
Office Action submitted in U.S. Appl. No. 09/498,667, dated May 5, 2000.
Office Action submitted in U.S. Appl. No. 09/706,525, dated Feb. 28, 2001.
Office Action submitted in U.S. Appl. No. 09/910,183, dated Aug. 23, 2002.
Office Action submitted in U.S. Appl. No. 09/910,183, dated May 29, 2003.
Notice of Allowance submitted in U.S. Appl. No. 09/910,183, dated Dec. 24, 2003.
Office Action submitted in U.S. Appl. No. 09/910,183, dated Feb. 2, 2005.
Notice of Allowance submitted in U.S. Appl. No. 09/910,183, dated Sep. 28, 2005.
Office Action submitted in U.S. Appl. No. 11/244,331, dated Dec. 22, 2006.
Office Action submitted in U.S. Appl. No. 11/821,259, dated May 9, 2008.
Office Action submitted in U.S. Appl. No. 11/821,259, dated Dec. 1, 2008.
Notice of Allowance submitted in U.S. Appl. No. 11/821,259, dated Aug. 20, 2009.
Office Action submitted in U.S. Appl. No. 12/632,608, dated Oct. 19, 2010.
Office Action submitted in U.S. Appl. No. 13/089,099, dated Sep. 8, 2011.
Non-Final Office Action submitted in U.S. Appl. No. 13/330,581, dated Mar. 28, 2013.
Final Office Action submitted in U.S. Appl. No. 13/330,581, dated Nov. 1, 2012.
Notice of Allowance submitted in U.S. Appl. No. 13/330,581, dated Dec. 17, 2012.

* cited by examiner

| loci | allelic designation | size (bp) | loci | allelic designation | size (bp) | loci | allelic designation | size (bp) | loci | allelic designation | size (bp) |
|---|---|---|---|---|---|---|---|---|---|---|---|
| TH01 | 4 | 150 | D8 | 7 | 157 | D18 | 8 | 266 | FGA (LMW) | 16.1 | 173 |
| | 5 | 154 | | 8 | 161 | | 9 | 270 | | 17 | 176 |
| | 6 | 158 | | 9 | 165 | | 10 | 274 | | 18 | 180 |
| | 7 | 162 | | 10 | 169 | | 11 | 278 | | 19 | 184 |
| | 8 | 166 | | 11 | 173 | | 12 | 282 | | 20 | 188 |
| | 9 | 170 | | 12 | 177 | | 13 | 286 | | 21 | 192 |
| | 9.3 | 173 | | 13 | 181 | | 14 | 290 | | 22 | 196 |
| | 10 | 174 | | 14 | 185 | | 15 | 294 | | 23 | 200 |
| | 11 | 178 | | 15 | 189 | | 16 | 298 | | 24 | 204 |
| | 13.3 | 189 | | 16 | 193 | | 17 | 302 | | 25 | 208 |
| D21 | 53 | 203 | | 17 | 197 | | 18 | 306 | | 26 | 212 |
| | 54 | 205 | | 18 | 201 | | 19 | 310 | | 27 | 216 |
| | 56 | 209 | | 19 | 205 | | 20 | 314 | | 28 | 220 |
| | 57 | 211 | VWA | 10 | 122 | | 21 | 318 | | 29 | 224 |
| | 59 | 215 | | 11 | 126 | | 22 | 322 | | 30 | 228 |
| | 61 | 219 | | 12 | 130 | | 23 | 326 | | 30.2 | 230 |
| | 63 | 223 | | 13 | 134 | | 24 | 330 | | 31.2 | 234 |

*FIGURE 1A*

| loci | allelic designation | size (bp) | loci | allelic designation | size (bp) | loci | allelic designation | size (bp) |
|---|---|---|---|---|---|---|---|---|
| | 65 | 227 | | 14 | 138 | | 32.2 | 238 |
| | 67 | 231 | | 15 | 142 | | 33.2 | 242 |
| | 68 | 233 | | 16 | 146 | | 34.2 | 246 |
| | 70 | 237 | | 17 | 150 | AMELO | X | 105 |
| | 72 | 241 | | 18 | 154 | | Y | 111 |
| | 74 | 245 | | 19 | 158 | | 42.2 | 278 |
| | 75 | 247 | | 20 | 162 | | 42.3 | 282 |
| | 77 | 251 | | 21 | 166 | | 44.2 | 286 |
| | 79 | 255 | | | | | 45.2 | 290 |
| | 81 | 259 | | | | | 46.2 | 294 |
| | | | | | | | 47.2 | 298 |
| | | | | | | | 48.2 | 302 |
| | | | | | | | 50.2 | 310 |

*FIGURE 1B*

HUMVWAF31/A sequences                              FIGURE 3A

10    TCTA TCTG TCTA (TCTG)$_4$ (TCTA)$_3$ (SEQ ID No: 1)
12    TCTA (TCTG)$_4$ (TCTA)$_7$ (SEQ ID No: 2)
13    (TCTA)$_2$ (TCTG)$_4$ (TCTA) TCCA (TCTA)$_3$ (TCCA)$_2$ T (SEQ ID No: 39)
(Note also that the 13 allele has an atypical 3' flanking
sequence (highlighted). The usual sequence is TCCA TCTA T.)

HUMTH01 sequences                                  FIGURE 3B 13.3  (TCAT)$_6$ CAT (TCAT)$_3$ TCGT$^{12th}$ TCAT (SEQ ID No: 4)

D2S1179 sequences                                  FIGURE 3C 7     (TCTA)$_8$ (SEQ ID No: 5)
19    (TCTA)$_2$ TCTG (TCTA)$_{16}$ (SEQ ID No: 6)

HUMFIBRA(FGA) Repeat Sequences                     FIGURE 3D 16.1  (TTTC)$_3$ TTTT TTCT (CTTT)$_6$ T (CTTT)$_3$ CTCC (TTCC)$_2$ (SEQ ID No: 7)
27    (TTTC)$_3$ TTTT TTCT (CTTT)$_{13}$ CCTT (CTTT)$_5$ CTCC (TTCC)$_2$ (SEQ ID No: 8)
30    (TTTC)$_3$ TTTT TTCT (CTTT)$_{16}$ CCTT (CTTT)$_5$ CTCC (TTCC)$_2$ (SEQ ID No: 9)
31.2  (TTTC)$_4$ TTTT TT (CTTT)$_{15}$ (CTTC)$_2$ (CTTT)$_3$ CTCC (TTCC)$_4$ (SEQ ID No: 10)
32.2  (TTTC)$_4$ TTTT TT (CTTT)$_{16}$ (CTTC)$_2$ (CTTT)$_3$ CTCC (TTCC)$_4$ (SEQ ID No: 11)
33.2  (TTTC)$_4$ TTTT TT (CTTT)$_{17}$ (CTTC)$_2$ (CTTT)$_3$ CTCC (TTCC)$_4$ (SEQ ID No: 12)
42.2  (TTTC)$_4$ TTTT TT (CTTT)$_6$ (CTGT)$_4$ (CTTT)$_{13}$ (CTTC)$_4$ (CTTT)$_3$
      CTCC (TTCC)$_4$ (SEQ ID No: 13)
43.2  (TTTC)$_4$ TTTT TT (CTTT)$_8$ (CTGT)$_5$ (CTTT)$_{13}$ (CTTC)$_4$ (CTTT)$_3$
      CTCC (TTCC)$_4$ (SEQ ID No: 14)
44.2  (TTTC)$_4$ TTTT TT (CTTT)$_{11}$ (CTGT)$_3$ (CTTT)$_{14}$ (CTTC)$_3$ (CTTT)$_3$
      CTCC (TTCC)$_4$ (SEQ ID No: 15)
45.2  (TTTC)$_4$ TTTT TT (CTTT)$_{10}$ (CTGT)$_5$ (CTTT)$_{12}$ (CTTC)$_4$ (CTTT)$_3$
      CTCC (TTCC)$_4$ (SEQ ID No: 16)
47.2  (TTTC)$_4$ TTTT TT (CTTT)$_{12}$ (CTGT)$_4$ (CTTT)$_{14}$ (CTTC)$_3$ (CTTT)$_3$
      CTCC (TTCC)$_4$ (SEQ ID No: 17)
48.2  (TTTC)$_4$ TTTT TT (CTTT)$_{14}$ (CTGT)$_3$ (CTTT)$_{14}$ (CTTC)$_4$ (CTTT)$_3$
      CTCC (TTCC)$_4$ (SEQ ID No: 18)

D21S11 alleles                                              FIGURE 3E 53   (TCTA)$_4$ (TCTG)$_6$ (TCTA)$_3$ TA(TCTA)$_3$ TCA (TCTA)$_2$ TCCATA
(TCTA)$_6$ TCGTCT (SEQ ID No: 19)

54   (TCTA)$_5$ (TCTG)$_6$ (TCTA)$_3$ TCA (TCTA)$_3$ TCCATA (TCTA)$_9$ TCGTCT (SEQ ID No: 20)

56   (TCTA)$_5$ (TCTG)$_6$ (TCTA)$_3$ TCA (TCTA)$_3$ TCCATA (TCTA)$_{10}$ TCGTCT (SEQ ID No: 21)

57   (TCTA)$_4$ (TCTG)$_6$ (TCTA)$_3$ TA (TCTA)$_3$ TCA (TCTA)$_2$ TCCATA
(TCTA)$_8$ TCGTCT (SEQ ID No: 22)

59   (TCTA)$_6$ (TCTG)$_5$ (TCTA)$_3$ TA (TCTA)$_3$ TCA (TCTA)$_2$ TCCATA
(TCTA)$_9$ TCGTCT (SEQ ID No: 23)

61   (TCTA)$_4$ (TCTG)$_6$ (TCTA)$_3$ TA (TCTA)$_3$ TCA (TCTA)$_2$ TCCATA
(TCTA)$_{10}$ TCGTCT (SEQ ID No: 24)

63   (TCTA)$_4$ (TCTG)$_6$ (TCTA)$_3$ TA (TCTA)$_3$ TCA (TCTA)$_2$ TCCATA
(TCTA)$_{11}$ TCGTCT (SEQ ID No: 25)

65   (TCTA)$_5$ (TCTG)$_5$ (TCTA)$_3$ TA (TCTA)$_3$ TCA (TCTA)$_2$ TCCATA
(TCTA)$_{11}$ TCGTCT (SEQ ID No: 26)

67   (TCTA)$_5$ (TCTG)$_6$ (TCTA)$_3$ TA (TCTA)$_3$ TCA (TCTA)$_2$ TCCATA
(TCTA)$_{12}$ TCGTCT (SEQ ID No: 27)

68   (TCTA)$_5$ (TCTG)$_6$ (TCTA)$_3$ TA (TCTA)$_3$ TCA (TCTA)$_2$ TCCATA
(TCTA)$_{11}$ TA TCTA TCGTCT (SEQ ID No: 28)

70   (TCTA)$_5$ (TCTG)$_6$ (TCTA)$_3$ TA (TCTA)$_3$ TCA (TCTA)$_2$ TCCATA
(TCTA)$_{12}$ TA TCTA TCGTCT (SEQ ID No: 29)

72   (TCTA)$_5$ (TCTG)$_6$ (TCTA)$_3$ TA (TCTA)$_3$ TCA (TCTA)$_2$ TCCATA
(TCTA)$_{13}$ TA TCTA TCGTCT (SEQ ID No: 30)

74   (TCTA)$_5$ (TCTG)$_6$ (TCTA)$_3$ TA (TCTA)$_3$ TCA (TCTA)$_2$ TCCATA
(TCTA)$_{14}$ TATCTA TCGTCT (SEQ ID No: 31)

75   (TCTA)$_{10}$ (TCTG)$_5$ (TCTA)$_3$ TA (TCTA)$_3$ TCA (TCTA)$_2$ TCCATA
(TCTA)$_{12}$ TCGTCT (SEQ ID No: 32)

77   (TCTA)$_{11}$ (TCTG)$_5$ (TCTA)$_3$ TA (TCTA)$_3$ TCA (TCTA)$_2$ TCCATA
(TCTA)$_{12}$ TCGTCT (SEQ ID No: 33)

79   (TCTA)$_{11}$ (TCTG)$_5$ (TCTA)$_3$ TA (TCTA)$_3$ TCA (TCTA)$_2$ TCCATA
(TCTA)$_{13}$ TCGTCT (SEQ ID No: 34)

81   (TCTA)$_{12}$ (TCTG)$_5$ (TCTA)$_3$ TA (TCTA)$_3$ TCA (TCTA)$_2$ TCCATA
(TCTA)$_{13}$ TCGTCT (SEQ ID No: 35)

D18S51 sequences                                            FIGURE 3F 8    (AGAA)$_8$ (SEQ ID No: 36)

FORENSIC IDENTIFICATION

CROSS-REFERENCE TO RELATED APPLICATIONS

This application is a continuation of U.S. application Ser. No. 13/330,581, filed Dec. 19, 2011, which is a continuation of U.S. application Ser. No. 13/089,099, filed Apr. 18, 2011 (abandoned), which is a continuation of U.S. patent application Ser. No. 12/632,608, filed Dec. 7, 2009 (abandoned), which is a continuation of U.S. patent application Ser. No. 11/821,259, filed Jun. 21, 2007, now U.S. Pat. No. 7,645,580, which is a continuation of U.S. patent application Ser. No. 11/244,331, filed Oct. 4, 2005 (abandoned), which is a continuation of U.S. patent application Ser. No. 09/910,183, filed Jul. 20, 2001, now U.S. Pat. No. 7,087,380, which is a continuation of U.S. patent application Ser. No. 09/706,525, filed Nov. 3, 2000 (abandoned), which is a continuation of U.S. patent application Ser. No. 09/498,567, filed Feb. 4, 2000 (abandoned), which is a continuation of U.S. patent application Ser. No. 09/107,029, filed Jun. 29, 1998 (abandoned), which claims priority to United Kingdom Application No. 9713597.4, filed Jun. 28, 1997, which for purposes of disclosure are each incorporated herein by specific reference in their entireties.

This application contains a Sequence Listing which has been submitted in ASCII format via EFS-Web and is hereby incorporated by reference in its entirety. Said ASCII copy, created on Jan. 23, 2013, is named 0051_0092_US10_Sequence Listing.txt and is 10776 bytes in size.

BACKGROUND OF THE INVENTION

1. The Field of the Invention

The present invention is concerned with improvements in and relating to forensic identification, particularly where based on DNA profiling.

2. The Relevant Technology

DNA profiling offers a versatile identification technique for a wide variety of applications including, anthropological, paternity and other forensic environments. The use of such profiling is significant in determining links, or their absence, between samples. Such samples might include those taken from known individuals and/or those taken from the scene of or linked to a crime.

DNA profiling based on the use of short tandem repeats (STR) or micro satellite loci is used in such applications. STR's are a class of polymorphic markers which consist of simple randomly repeated sequences of between 1 and 6 base pairs in length. STR's in the non-coding part of the genome are generally considered.

In the human genome STR's occur every 6 to 10 kilo bases along the DNA. The length, however, varies greatly between individuals due to mutation and provides identifying characteristics as a result.

A variety of DNA profiling systems exist, including single locus analysis and multiple locus analysis where a number of STR loci are simultaneously amplified.

In analyzing the results from an unknown sample it is generally considered against a ladder marker consisting of alleles derived from actual samples. The allelic ladder provides a reference point and allows correspondence of alleles to be identified clearly.

SUMMARY OF THE INVENTION

The present invention provides new alleles and new ladders incorporating them for a variety of loci. The present invention offers an improved range and coverage of markers as a result. The ladders include a number of rare alleles offering improved identification of the alleles in an unknown sample.

According to a first aspect of the invention we provide an allelic ladder mixture comprising one or more of the following allelic ladders:

i) an allelic ladder for locus HUMVWFA31/A comprising one or more of alleles comprising or consisting of sequences:

$$\text{TCTA TCTG TCTA } (\text{TCTG})_4 \text{ } (\text{TCTA})_3; \quad (\text{SEQ ID NO: 1})$$

$$\text{TCTA } (\text{TCTG})_4 \text{ } (\text{TCTA})_7; \quad (\text{SEQ ID NO: 2})$$

or $$(\text{TCTA})_2 \text{ } (\text{TCTG})_4 \text{ } (\text{TCTA})_3 \text{ TCCA } (\text{TCTA})_3 \quad (\text{SEQ ID NO: 3})$$

or at least 75% homologous thereto;

ii) an allelic ladder for locus HUMTHO1 comprising or consisting of sequence:

$$(\text{TCAT})_4 \text{ CAT } (\text{TCAT})_7 \text{ TCGT TCAT}; \quad (\text{SEQ ID NO: 4})$$

or at least 75% homologous thereto;

iii) are allelic ladder for locus D8S1179 comprising one or more of alleles:

$$(\text{TCTA})_8; \quad (\text{SEQ ID NO: 5})$$

$$(\text{TCTA})_2 \text{ TCTG}(\text{TCTA})_{16} \quad (\text{SEQ ID NO: 6})$$

or at least 75% homologous thereto;

iv) an allelic ladder for locus HUMFIBRA/FGA comprising one or more of alleles comprising or consisting of the sequences:

$$(\text{TTTC})_3 \text{ TTTT TTCT } (\text{CTTT})_5 \text{ T } (\text{CTTT})_3 \text{ CTCC } (\text{TTCC})_2; \quad (\text{SEQ ID NO: 7})$$

$$(\text{TTTC})_3 \text{ TTTT TTCT } (\text{CTTT})_{13} \text{ CCTT } (\text{CTTT})_5 \text{ CTCC } (\text{TTCC})_2; \quad (\text{SEQ ID NO: 8})$$

$$(\text{TTTC})_3 \text{ TTTT TTCT } (\text{CTTT})_{16} \text{ CCTT } (\text{CTTT})_5 \text{ CTCC } (\text{TTCC})_2; \quad (\text{SEQ ID NO: 9})$$

$$(\text{TTTC})_4 \text{ TTTT TT } (\text{CTTT})_{15} \text{ } (\text{CTTC})_3 \text{ } (\text{CTTT})_3 \text{ CTCC } (\text{TTCC})_4; \quad (\text{SEQ ID NO: 10})$$

-continued (SEQ ID NO: 11)
(TTTC)$_4$ TTTT TT (CTTT)$_{16}$ (CTTC)$_3$ (CTTT)$_3$ CTCC (TTCC)$_4$;

(SEQ ID NO: 12)
(TTTC)$_4$ TTTT TT (CTTT)$_{17}$ (CTTC)$_3$ (CTTT)$_3$ CTCC (TTCC)$_4$;

(SEQ ID NO: 13)
(TTTC)$_4$ TTTT TT (CTTT)$_8$ (CTGT)$_4$ (CTTT)$_{13}$ (CTTC)$_4$ (CTTT)$_3$ CTCC (TTCC)$_4$;

(SEQ ID NO: 14)
(TTTC)$_4$ TTTT TT (CTTT)$_8$ (CTGT)$_5$ (CTTT)$_{13}$ (CTTC)$_4$ (CTTT)$_3$ CTCC (TTCC)$_4$;

(SEQ ID NO: 15)
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$;

(SEQ ID NO: 16)
(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$;

(SEQ ID NO: 17)
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$;
or (SEQ ID NO: 18)
(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$;

or at least 75% homologous thereto;
  v) an allelic ladder for locus D21S11 comprising one or more of alleles comprising or consisting of sequences:

(SEQ ID NO: 19)
(TCTA)$_4$ (TCTG)$_6$ (TCTA)$_3$ TA(TCTA)$_3$ TCA (TCTA)$_2$ TCCATA (TCTA)$_6$ TCGTCT;

(SEQ ID NO: 20)
(TCTA)$_5$ (TCTG)$_6$ (TCTA)$_3$ TCA (TCTA)$_2$ TCCATA (TCTA)$_9$ TCGTCT;

(SEQ ID NO: 21)
(TCTA)$_5$ (TCTG)$_6$ (TCTA)$_3$ TCA (TCTA)$_2$ TCCATA (TCTA)$_{10}$ TCGTCT;

(SEQ ID NO: 22)
(TCTA)$_4$ (TCTG)$_6$ (TCTA)$_3$ TA (TCTA)$_3$ TCA (TCTA)$_2$ TCCATA (TCTA)$_8$ TCGTCT;

(SEQ ID NO: 23)
(TCTA)$_5$ (TCTG)$_5$ (TCTA)$_3$ TA (TCTA)$_3$ TCA (TCTA)$_2$ TCCATA (TCTA)$_9$ TCGTCT;

(SEQ ID NO: 24)
(TCTA)$_4$ (TCTG)$_6$ (TCTA)$_3$ TA (TCTA)$_3$ TCA (TCTA)$_2$ TCCATA (TCTA)$_{10}$ TCGTCT;

(SEQ ID NO: 25)
(TCTA)$_4$ (TCTG)$_6$ (TCTA)$_3$ TA (TCTA)$_3$ TCA (TCTA)$_2$ TCCATA (TCTA)$_{11}$ TCGTCT;

(SEQ ID NO: 26)
(TCTA)$_6$ (TCTG)$_5$ (TCTA)$_3$ TA (TCTA)$_3$ TCA (TCTA)$_2$ TCCATA (TCTA)$_{11}$ TCGTCT;

(SEQ ID NO: 27)
(TCTA)$_5$ (TCTG)$_6$ (TCTA)$_3$ TA (TCTA)$_3$ TCA (TCTA)$_2$ TCCATA (TCTA)$_{12}$ TCGTCT;

(SEQ ID NO: 28)
(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT;

(SEQ ID NO: 29)
(TCTA)$_5$ (TCTG)$_6$ (TCTA)$_3$ TA (TCTA)$_3$ TCA (TCTA)$_3$ TCCATA (TCTA)$_{12}$ TA TCTA TCGTCT;

(SEQ ID NO: 30)
(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT;

(SEQ ID NO: 31)
(TCTA)$_5$ (TCTG)$_6$ (TCTA)$_3$ TA (TCTA)$_3$ TCA (TCTA)$_2$ TCCATA (TCTA)$_{14}$ TATCTA TCGTCT;

-continued

```
                                                     (SEQ ID NO: 32)
(TCTA)₁₀ (TCTG)₅ (TCTA)₃ TA (TCTA)₃ TCA (TCTA)₂ TCCATA (TCTA)₁₂ TCGTCT;

(SEQ ID NO: 33)
(TCTA)₁₁ (TCTG)₅ (TCTA)₃ TA (TCTA)₃ TCA (TCTA)₂ TCCATA (TCTA)₁₂ TCGTCT;

(SEQ ID NO: 34)
(TCTA)₁₁ (TCTG)₅ (TCTA)₃ TA (TCTA)₃ TCA (TCTA)₂ TCCATA (TCTA)₁₃ TCGTCT;
or (SEQ ID NO: 35)
(TCTA)₁₃ (TCTG)₅ (TCTA)₃ TA (TCTA)₃ TCA (TCTA)₂ TCCATA (TCTA)₁₂ TCGTCT;
``` or at least 75% homologous thereto;

vi) an allelic ladder for locus D18S51 comprising an allele comprising or consisting of sequence:

(AGAA)₈ (SEQ ID NO: 36); or at least 75% homologous thereto.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTHO1; D8S1179, HUMFIBRA/FGA, D21511 and D18S51. Preferably the mixture includes allelic ladders for at least four of these loci. In its most preferred form the mixture includes allelic ladders for all of these loci.

Preferably the mixture includes an amelogenin sex test.

Preferably one or more of the allelic ladders in the mixture includes at least 7 alleles and more preferably at least 12 alleles. Preferably a plurality, and particularly all, of the allelic ladders of the mixture include at least 8 and more preferably at least 10 alleles.

Preferably one or more or all of the ladders, if present in the mixture may be provided such that: the HUMVWFA31/A allelic ladder includes at least 9, more preferably 11 and ideally 12 alleles; the HUMTHO1 allelic ladder includes at least 7, more preferably 9 and ideally 10 alleles; the D8S1179 allelic ladder includes at least 9, more preferably 12 and ideally 13 alleles; the HUMFIBRA/FGA allele ladder includes at least 18, more preferably OQ 26 and ideally 28 alleles or is present as HUMFIBRA/FGA/LW and HUMFIBRA/FGA/HW with the HUMFIBRA/FGA/LW ladder including at least 16 more preferably 18 and ideally 20 alleles, the HUMFIBRA/FGA/HW ladder including at least 6, more preferably at least 7 and ideally 8 alleles; the D21S11 allelic ladder includes at least 14, more preferably 16 and ideally 17 alleles; and the D18S51 ladder includes at least 15, more preferably 19 and ideally 20 alleles.

Preferably one or more of the allelic ladders in the mixture comprises at least 4 pairs of alleles 4 base pairs from each other. More preferably at least 10 pairs, and ideally at least 12 pairs of alleles are so provided. Preferably one or more or all the allele ladders, if present in the mixture, may be provided such that: the HUMVWFA31/A allele ladder includes at least 7, more preferably 10 and ideally 11 pairs of alleles 4 base pairs from each other; the HUMTHO1 allele ladder includes at least 5, more preferably 6 and ideally 7 pairs of alleles 4 base pairs from each other; the D8S1179 allelic ladder includes at least 8, more preferably 11 and ideally 12 pairs of alleles 4 base pairs from each other; the HUMFIBRA/FGA allele ladder includes at least 17, more preferably 20 and ideally 23 pairs of alleles 4 base pairs from each other; the D21S11 allele ladder includes at least 3 and ideally 4 pairs of alleles 4 base pairs from each other; and the D18S51 ladder includes at least 13, more preferably 18 and ideally 19 pairs of alleles 4 base pairs from each other. The D21S11 allele ladder may, or may further include, at least 8, more preferably 11 and ideally 12 pairs of alleles 8 base pairs from each other.

Preferably the allele sequences have at least 85% homogeneity with the listed sequences. More preferable levels of even 90% or at least 95% may be provided. Ideally the exact sequences listed are included within the alleles. In their most preferred form the alleles consist of the listed sequences.

The alleles may further include flanking sequences, i.e., between the primer and STR.

Preferably the HUMVWFA31/A ladder includes alleles ranging from 130, more preferably 126 and ideally 122 base pairs upwards and/or from 166 base pairs downwards. Preferably the HUMTHO1 ladder includes alleles ranging from 150 base pairs upwards and or 189 base pairs downwards. Preferably the D8S1179 ladder includes alleles ranging from 157 base pairs upwards and/or 201, and more preferably 205 base pairs downwards. Preferably the HUMFIBRA/FGA ladder includes alleles ranging from 173 base pairs upwards and/or 298, more preferably 302 and ideally 310 base pairs downwards. Preferably the D21S11 ladder includes alleles ranging from 203 base pairs upwards and/or 255 or more preferably 259 base pairs downwards. Preferably the D18S51 ladder includes alleles ranging from 270 or more preferably 266 base pairs upwards and/or 326 or 330 or 334 or 338 or even 342 downwards.

According to a second aspect of the invention we provide an allelic ladder mixture comprising an allelic ladder for one or more of the following loci, with lowest molecular weight allele and/or uppermost molecular weight allele as follows

| Locus | Low MW allele | High MW allele |
|---|---|---|
| a) HUMVWFA31/A | 10 | 21 |
| b) HUMTH01 | 4 | 13.3 |
| c) D8S1179 | 7 | 19 |
| d) HUMFIBRA/FGA | 16.1 | 50.2 |
| e) D21S11 | 53 | 81 |
| f) D18S51 | 8 | 27 |

Preferably one or more of the loci ladders have both the upper and lower limits specified. Preferably all the loci ladders have the full ranges listed.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTHO1, D8S1179, HUMFIBRA/FGA, D21S11 and D18S51. Preferably the mixture includes allelic ladders for at least four of these loci. In its most preferred form the mixture includes allelic ladders for all of these loci.

The intervals of alleles in the ladders and/or number of alleles in the ladders may be as specified in the first aspect of the invention. This aspect may include any of the other features specified elsewhere in the application.

The ladder mixtures of the first and/or second aspect of the invention may further include one or more of PARR buffer, primer(s), or Taq polymerase.

According to a third aspect of the invention we provide a method of analysing one or more samples comprising:—
a) obtaining genomic DNA from the sample;
b) amplifying the DNA;
c) obtaining an indication of one or more of the constituent parts of the sample; and comparing the indications with an allelic ladder mixture comprising one or more of the following allelic ladders:
i) an allelic ladder for locus HUMVWFA31/A comprising one or more of alleles comprising or consisting of sequences:

$$\text{TCTA TCTG TCTA (TCTG)}_4 \text{ (TCTA)}_3; \quad \text{(SEQ ID NO: 1)}$$

$$\text{TCTA (TCTG)}_4 \text{ (TCTA)}_7; \quad \text{(SEQ ID NO: 2)}$$
or $$\text{(TCTA)}_2 \text{ (TCTG)}_4 \text{ (TCTA)}_3 \text{ TCCA (TCTA)}_3 \quad \text{(SEQ ID NO: 3)}$$

ii) an allelic ladder for locus HUMTHO1 comprising or consisting of sequence:

$$\text{(TCAT)}_4 \text{ CAT (TCAT)}_7 \text{ TCGT TCAT}; \quad \text{(SEQ ID NO: 4)}$$

iii) an allelic ladder for locus D8S1179 comprising one or more of alleles comprising or consisting of sequences:

$$\text{(TCTA)}_8; \quad \text{(SEQ ID NO 5)}$$
or $$\text{(TCTA)}_2 \text{ TCTG (TCTA)}_{16}; \quad \text{(SEQ ID NO: 6)}$$

iv) an allelic ladder for locus HUMFIBRA/FGA comprising one or more of alleles comprising, or consisting of the sequences:

$$\text{(TTTC)}_3 \text{ TTTT TTCT (CTTT)}_5 \text{ T (CTTT)}_3 \text{ CTCC (TTCC)}_2; \quad \text{(SEQ ID NO: 7)}$$

$$\text{(TTTC)}_3 \text{ TTTT TTCT (CTTT)}_{13} \text{ CCTT (CTTT)}_5 \text{ CTCC (TTCC)}_2; \quad \text{(SEQ ID NO: 8)}$$

$$\text{(TTTC)}_3 \text{ TTTT TTCT (CTTT)}_{16} \text{ CCTT (CTTT)}_5 \text{ CTCC (TTCC)}_2; \quad \text{(SEQ ID NO: 9)}$$

$$\text{(TTTC)}_4 \text{ TTTT TT (CTTT)}_{15} \text{ (CTTC)}_3 \text{ (CTTT)}_3 \text{ CTCC (TTCC)}_4; \quad \text{(SEQ ID NO: 10)}$$

$$\text{(TTTC)}_4 \text{ TTTT TT (CTTT)}_{16} \text{ (CTTC)}_3 \text{ (CTTT)}_3 \text{ CTCC (TTCC)}_4; \quad \text{(SEQ ID NO: 11)}$$

$$\text{(TTTC)}_4 \text{ TTTT TT (CTTT)}_{17} \text{ (CTTC)}_3 \text{ (CTTT)}_3 \text{ CTCC (TTCC)}_4; \quad \text{(SEQ ID NO: 12)}$$

$$\text{(TTTC)}_4 \text{ TTTT TT (CTTT)}_8 \text{ (CTGT)}_4 \text{ (CTTT)}_{13} \text{ (CTTC)}_4 \text{ (CTTT)}_3 \text{ CTCC (TTCC)}_4; \quad \text{(SEQ ID NO: 13)}$$

$$\text{(TTTC)}_4 \text{ TTTT TT (CTTT)}_8 \text{(CTGT)}_5 \text{ (CTTT)}_{13} \text{ (CTTC)}_4 \text{ (CTTT)}_3 \text{ CTCC (TTCC)}_4; \quad \text{(SEQ ID NO: 14)}$$

$$\text{(TTTC)}_4 \text{ TTTT TT (CTTT)}_{11} \text{ (CTGT)}_3 \text{ (CTTT)}_{14} \text{ (CTTC)}_3 \text{ (CTTT)}_3 \text{ CTCC (TTCC)}_4; \quad \text{(SEQ ID NO: 15)}$$

$$\text{(TTTC)}_4 \text{ TTTT TT (CTTT)}_{10} \text{ (CTGT)}_5 \text{ (CTTT)}_{13} \text{ (CTTC)}_4 \text{ (CTTT)}_3 \text{ CTCC (TTCC)}_4; \quad \text{(SEQ ID NO: 16)}$$

$$\text{(TTTC)}_4 \text{ TTTT TT (CTTT)}_{12} \text{ (CTGT)}_5 \text{ (CTTT)}_{14} \text{ (CTTC)}_3 \text{ (CTTT)}_3 \text{ CTCC (TTCC)}_4; \quad \text{(SEQ ID NO: 17)}$$
or $$\text{(TTTC)}_4 \text{ TTTT TT (CTTT)}_{14} \text{ (CTGT)}_3 \text{ (CTTT)}_{14} \text{ (CTTC)}_4 \text{ (CTTT)}_3 \text{ CTCC (TTCC)}_4; \quad \text{(SEQ ID NO: 18)}$$

v) an allelic ladder for locus D21S11 comprising one or more of alleles comprising or consisting of sequences:

$$\text{(TCTA)}_4 \text{ (TCTG)}_6 \text{ (TCTA)}_3 \text{ TA(TCTA)}_3 \text{ TCA (TCTA)}_2 \text{ TCCATA (TCTA)}_6 \text{ TCGTCT}; \quad \text{(SEQ ID NO: 19)}$$

$$\text{(TCTA)}_5 \text{ (TCTG)}_6 \text{ (TCTA)}_3 \text{ TCA (TCTA)}_2 \text{ TCCATA (TCTA)}_9 \text{ TCGTCT}; \quad \text{(SEQ ID NO: 20)}$$

$$\text{(TCTA)}_5 \text{ (TCTG)}_6 \text{ (TCTA)}_3 \text{ TCA (TCTA)}_2 \text{ TCCATA (TCTA)}_{10} \text{ TCGTCT}; \quad \text{(SEQ ID NO: 21)}$$

(SEQ ID NO: 22)
(TCTA)$_4$ (TCTG)$_6$ (TCTA)$_3$ TA (TCTA)$_3$ TCA (TCTA)$_2$ TCCATA (TCTA)$_8$ TCGTCT;

(SEQ ID NO: 23)
(TCTA)$_5$ (TCTG)$_5$ (TCTA)$_3$ TA (TCTA)$_3$ TCA (TCTA)$_2$ TCCATA (TCTA)$_9$ TCGTCT;

(SEQ ID NO: 24)
(TCTA)$_4$ (TCTG)$_6$ (TCTA)$_3$ TA (TCTA)$_3$ TCA (TCTA)$_2$ TCCATA (TCTA)$_{10}$ TCGTCT;

(SEQ ID NO: 25)
(TCTA)$_4$ (TCTG)$_6$ (TCTA)$_3$ TA (TCTA)$_3$ TCA (TCTA)$_2$ TCCATA (TCTA)$_{11}$ TCGTCT;

(SEQ ID NO: 26)
(TCTA)$_6$ (TCTG)$_5$ (TCTA)$_3$ TA (TCTA)$_3$ TCA (TCTA)$_2$ TCCATA (TCTA)$_{11}$ TCGTCT;

(SEQ ID NO: 27)
(TCTA)$_5$ (TCTG)$_6$ (TCTA)$_3$ TA (TCTA)$_3$ TCA (TCTA)$_2$ TCCATA (TCTA)$_{12}$ TCGTCT;

(SEQ ID NO: 28)
(TCTA)$_5$ (TCTG)$_6$ (TCTA)$_3$ TA (TCTA)$_3$ TCA (TCTA)$_2$ TCCATA (TCTA)$_{11}$ TATCTA
TCGTCT;

(SEQ ID NO: 29)
(TCTA)$_5$ (TCTG)$_6$ (TCTA)$_3$ TA (TCTA)$_3$ TCA (TCTA)$_2$ TCCATA (TCTA)$_{12}$ TATCTA
TCGTCT;

(SEQ ID NO: 30)
(TCTA)$_5$ (TCTG)$_6$ (TCTA)$_3$ TA (TCTA)$_3$ TCA (TCTA)$_2$ TCCATA (TCTA)$_{13}$ TATCTA
TCGTCT;

(SEQ ID NO: 31)
(TCTA)$_5$ (TCTG)$_6$ (TCTA)$_3$ TA (TCTA)$_3$ TCA (TCTA)$_2$ TCCATA (TCTA)$_{14}$ TATCTA
TCGTCT;

(SEQ ID NO: 32)
(TCTA)$_{10}$ (TCTG)$_5$ (TCTA)$_3$ TA (TCTA)$_3$ TCA (TCTA)$_2$ TCCATA (TCTA)$_{12}$ TCGTCT;

(SEQ ID NO: 33)
(TCTA)$_{11}$ (TCTG)$_5$ (TCTA)$_3$ TA (TCTA)$_3$ TCA (TCTA)$_2$ TCCATA (TCTA)$_{12}$ TCGTCT;

(SEQ ID NO: 34)
(TCTA)$_{11}$ (TCTG)$_5$ (TCTA)$_3$ TA (TCTA)$_3$ TCA (TCTA)$_2$ TCCATA (TCTA)$_{13}$ TCGTCT;
or (SEQ ID NO: 35)
(TCTA)$_{13}$ (TCTG)$_5$ (TCTA)$_3$ TA (TCTA)$_3$ TCA (TCTA)$_2$ TCCATA (TCTA)$_{12}$ TCGTCT;

vi) an allelic ladder for locus D18551 comprising an allele comprising or consisting of sequence:

(AGAA)$_8$;           (SEQ ID NO: 36)

including allelic ladders or alleles 75% homologous thereto.

The allelic ladder mixture may possess other features specified in the first or second aspects of the invention or elsewhere in this application.

Preferably the DNA sample is one or more of a sample taken from the scene of a crime, a sample associated with the scene of a crime, a sample obtained from a suspect, a sample obtained from a human under consideration (for instance for paternity or maternity analysis) or a reference sample. The sample may be in the form of blood, hair, skin or bodily fluid.

Preferably the sample is amplified using a polymerase chain reaction. Preferably primers for one or more of loci HUMVWFA31/A, HUMTHO1, D8S1179, HUMFIBRA/FGA, D21511 or D18551 are employed. The primers may be dye or otherwise labelled.

According to a fourth aspect of the invention we provide one or more alleles comprising or consisting of sequences:

(SEQ ID NO: 1)
TCTA TCTG TCTA (TCTG)$_4$ (TCTA)$_3$;

(SEQ ID NO: 2)
TCTA (TCTG)$_4$ (TCTA)$_7$;

(SEQ ID NO: 3)
(TCTA)$_2$ (TCTG)$_4$ (TCTA)$_3$ TCCA (TCTA)$_3$;

-continued (TCAT)$_4$ CAT (TCAT)$_7$ TCGT TCAT; (SEQ ID NO: 4)

(TCTA)$_8$; (SEQ ID NO: 5)

(TCTA)$_2$ TCTG (TCTA)$_{16}$; (SEQ ID NO: 6)

(TTTC)$_3$ TTTT TTCT (CTTT)$_5$ T (CTTT)$_3$ CTCC (TTCC)$_2$; (SEQ ID NO: 7)

(TTTC)$_3$ TTTT TTCT (CTTT)$_{13}$ CCTT (CTTT)$_5$ CTCC (TTCC)$_2$; (SEQ ID NO: 8)

(TTTC)$_3$ TTTT TTCT (CTTT)$_{16}$ CCTT (CTTT)$_5$ CTCC (TTCC)$_2$; (SEQ ID NO: 9)

(TTTC)$_4$ TTTT TT (CTTT)$_{15}$ (CTTC)$_3$ (CTTT)$_3$ CTCC (TTCC)$_4$; (SEQ ID NO: 10)

(TTTC)$_4$ TTTT TT (CTTT)$_{16}$ (CTTC)$_3$ (CTTT)$_3$ CTCC (TTCC)$_4$; (SEQ ID NO: 11)

(TTTC)$_4$ TTTT TT (CTTT)$_{17}$ (CTTC)$_3$ (CTTT)$_3$ CTCC (TTCC)$_4$; (SEQ ID NO: 12)

(TTTC)$_4$ TTTT TT (CTTT)$_8$ (CTGT)4 (CTTT)$_{13}$ (CTTC)$_4$ (CTTT)$_3$ CTCC (TTCC)$_4$; (SEQ ID NO: 13)

(TTTC)$_4$ TTTT TT (CTTT)$_8$ (CTGT)$_5$ (CTTT)$_{13}$ (CTTC)$_4$ (CTTT)$_3$ CTCC (TTCC)$_4$; (SEQ ID NO: 14)

(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$; (SEQ ID NO: 15)

(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$; (SEQ ID NO: 16)

(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$; (SEQ ID NO: 17)

(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$; (SEQ ID NO: 18)

(TCTA)$_4$ (TCTG)$_6$ (TCTA)$_3$ TA(TCTA)$_3$ TCA (TCTA)$_2$ TCCATA (TCTA)$_6$ TCGTCT; (SEQ ID NO: 19)

(TCTA)$_5$ (TCTG)$_6$ (TCTA)$_3$ TCA (TCTA)$_2$ TCCATA (TCTA)$_9$ TCGTCT; (SEQ ID NO: 20)

(TCTA)$_5$ (TCTG)$_6$ (TCTA)$_3$ TCA (TCTA)$_2$ TCCATA (TCTA)$_{10}$ TCGTCT; (SEQ ID NO: 21)

(TCTA)$_4$ (TCTG)$_6$ (TCTA)$_3$ TA (TCTA)$_3$ TCA (TCTA)$_2$ TCCATA (TCTA)$_8$ TCGTCT; (SEQ ID NO: 22)

(TCTA)$_5$ (TCTG)$_5$ (TCTA)$_3$ TA (TCTA)$_3$ TCA (TCTA)$_2$ TCCATA (TCTA)$_9$ TCGTCT; (SEQ ID NO: 23)

(TCTA)$_4$ (TCTG)$_6$ (TCTA)$_3$ TA (TCTA)$_3$ TCA (TCTA)$_2$ TCCATA (TCTA)$_{10}$ TCGTCT; (SEQ ID NO: 24)

(TCTA)$_4$ (TCTG)$_6$ (TCTA)$_3$ TA (TCTA)$_3$ TCA (TCTA)$_2$ TCCATA (TCTA)$_{11}$ TCGTCT; (SEQ ID NO: 25)

(TCTA)$_6$ (TCTG)$_5$ (TCTA)$_3$ TA (TCTA)$_3$ TCA (TCCA)$_2$ TCCATA (TCTA)$_{11}$ TCGTCT; (SEQ ID NO: 26)

(TCTA)$_5$ (TCTG)$_6$ (TCTA)$_3$ TA (TCTA)$_3$ TCA (TCTA)$_2$ TCCATA (TCTA)$_{12}$ TCGTCT; (SEQ ID NO: 27)

(TCTA)$_5$ (TCTG)$_6$ (TCTA)$_3$ TA (TCTA)$_3$ TCA (TCTA)$_2$ TCCATA (TCTA)$_{11}$ TATCTA TCGTCT; (SEQ ID NO: 28)

-continued (SEQ ID NO: 29)
(TCTA)$_5$ (TCTG)$_6$ (TCTA)$_3$ TA (TCTA)$_3$ TCA (TCTA)$_2$ TCCATA (TCTA)$_{12}$ TATCTA
TCGTCT;

(SEQ ID NO: 30)
(TCTA)$_5$ (TCTG)$_6$ (TCTA)$_3$ TA (TCTA)$_3$ TCA (TCTA)$_2$ TCCATA (TCTA)$_{13}$ TATCTA
TCGTCT;

(SEQ ID NO: 31)
(TCTA)$_5$ (TCTG)$_6$ (TCTA)$_3$ TA (TCTA)$_3$ TCA (TCTA)$_2$ TCCATA (TCTA)$_{14}$ TATCTA
TCGTCT;

(SEQ ID NO: 32)
(TCTA)$_{10}$ (TCTG)$_5$ (TCTA)$_3$ TA (TCTA)$_3$ TCA (TCTA)$_2$ TCCATA (TCTA)$_{12}$ TCGTCT;

(SEQ ID NO: 33)
(TCTA)$_{11}$ (TCTG)$_5$ (TCTA)$_3$ TA (TCTA)$_3$ TCA (TCTA)$_2$ TCCATA (TCTA)$_{12}$ TCGTCT;

(SEQ ID NO: 34)
(TCTA)$_{11}$ (TCTG)$_5$ (TCTA)$_3$ TA (TCTA)$_3$ TCA (TCTA)$_2$ TCCATA (TCTA)$_{13}$ TCGTCT;

(SEQ ID NO: 35)
(TCTA)$_{13}$ (TCTG)$_5$ (TCTA)$_3$ TA (TCTA)$_3$ TCA (TCTA)2 TCCATA (TCTA)$_{12}$ TCGTCT;
or (SEQ ID NO: 36)
(AGAA)$_8$;

or at least 75% homologous thereto.

/Preferably the alleles are provided purified from alleles other than those of HUMVWFA31/A HUMTHO1, D8S1179, HUMFIBRA/FGA, D21511, D18551 or AMG loci.

According to a fifth aspect of the invention we provide the use of an allelic ladder according to the first aspect of the invention and/or an allele according to the fourth aspect of the invention for comparison with a DNA analysis result.

The analysis may be a DNA profile of a sample. The profile may be based on analysis of one or more loci, in particular including one or more of HUMVWFA31/A, HUMTHO1, D8S1179, HUMFIBRA/FGA, D21511, D18551 or AMG. The sample may be from the scene of a crime, associated with the scene of a crime or comprise a bodily fluid sample. The sample may be used to compare two or more individuals, or samples arising therefrom, for instance in paternity and/or maternity analysis.

According to a sixth aspect of the invention we provide a method of producing an allelic ladder or mixture thereof by subjecting the ladders of the first, second or fourth aspects of the invention to PCR.

BRIEF DESCRIPTION OF THE DRAWINGS

The invention will now be described, by way of example only, and with reference to the accompanying figure in which:

FIGS. 1a and 1b illustrates the locus, allele designation and size for an embodiment of the invention;

FIG. 3a shows the sequence of selected alleles forming the HUMVWFA31/A ladder (SEQ ID NOS 1-2 and 39, respectively, in order of appearance);

FIG. 3b shows the sequence of selected alleles forming the HUMTHO1 ladder (SEQ ID NO: 4);

FIG. 3c shows the sequence of selected alleles forming the D8S1179 ladder (SEQ ID NOS 5-6, respectively, in order of appearance);

FIG. 3d shows the sequence of selected alleles forming the HUMFIBRA ladder (SEQ ID NOS 7-18, respectively, in order of appearance);

FIG. 3e shows the sequence of selected alleles forming the D21S11 ladder (SEQ ID NOS 19-35, respectively, in order of appearance); and FIG. 3f shows the sequence of selected alleles forming the D18S51 ladder (SEQ ID NO: 36).

DETAILED DESCRIPTION OF THE PREFERRED EMBODIMENTS

An allelic ladder mixture illustrative of the present invention is provided for loci HUMTHO1, D21S11, D8S1179, HUMVWFA31/A, HUMFIBRA/FGA and amelogenin sex test. The loci nomenclature is standard, corresponding to that used in the GENEBANK database.

The ladder mixture includes a significant number of alleles fair each locus so as to provide a base line for comparison across a wide range. The loci, allelic designation and base pair sizes for the mixture are shown in FIGS. 1a and 1b. The nomenclature for the loci is discussed in Gill et al. 1996 Int. Journal Leg. Med. 109 14-22.

The allelic ladder mixture was presented in PARR buffer (containing Tris and 1.5 mM Mg ions at pH8.0) obtained from Cambio, primers obtained from Oswell and Taq polymerase from Perkin Elmer.

Figure 2A:
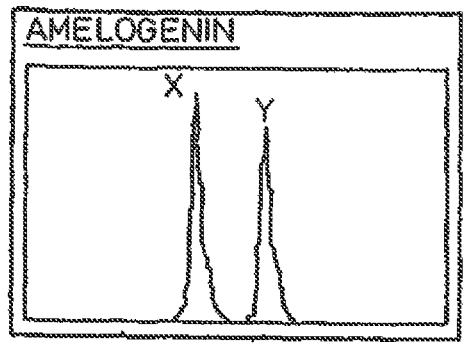
FIG. 2a shows an electrophoretogram of the allelic ladder for Amelogenin (AMG)
Figure 2B:
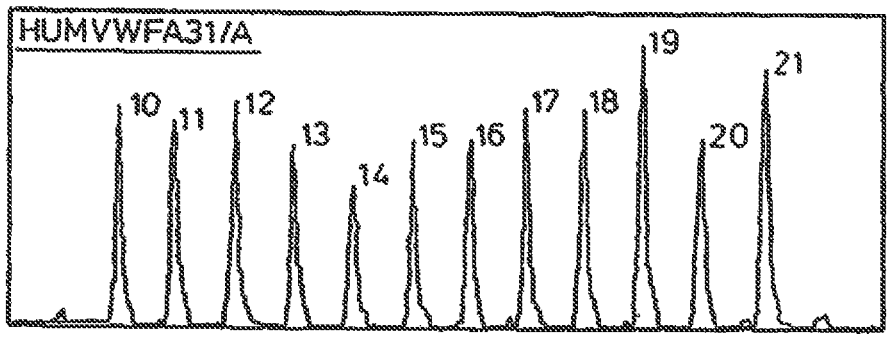
FIG. 2b shows an electrophoretogram of the allelic ladder for HUMVWFA31/A.
Figure 2C:
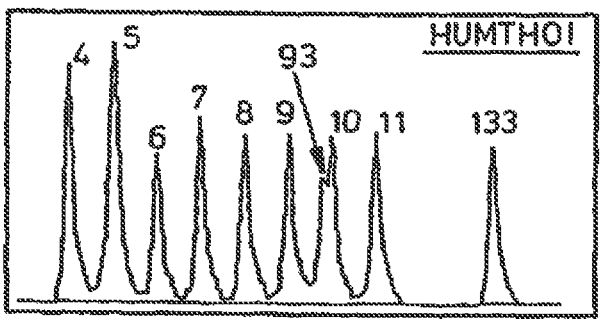
FIG. 2c shows an electrophoretogram of the allelic ladder for HUMTHO1.
Figure 2D:
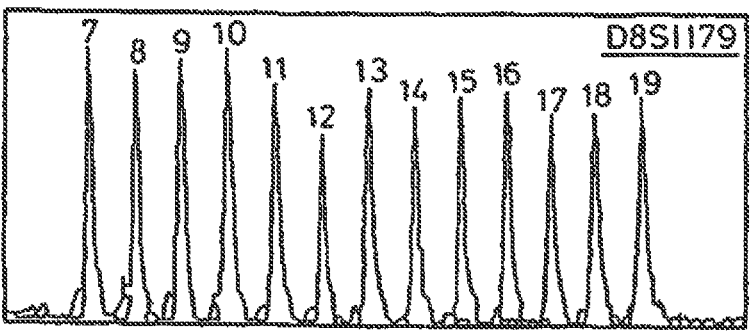
FIG. 2d shows an electrophoretogram of the allelic ladder for D8S1179.
Figure 2E:
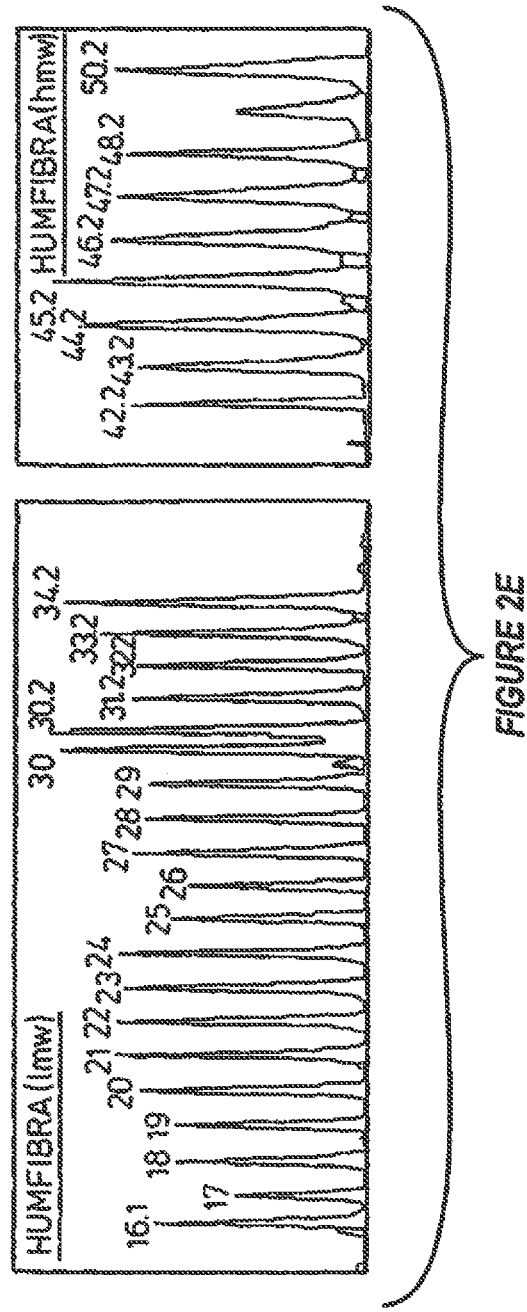
FIG. 2e shows an electrophoretogram of the allelic ladder for HUMFIBRA, low and high molecular weights.
Figure 2F:
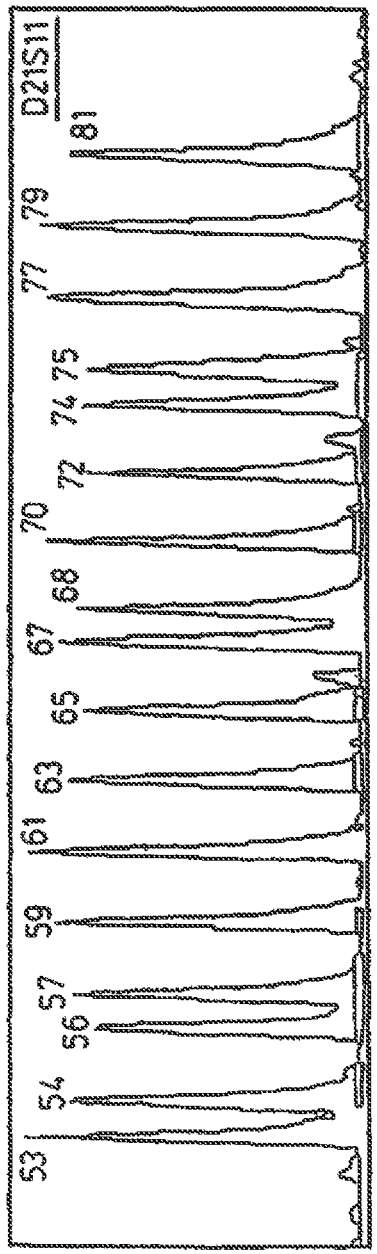
FIG. 2f shows an electrophoretogram of the allelic ladder for D21511.
Figure 2G:
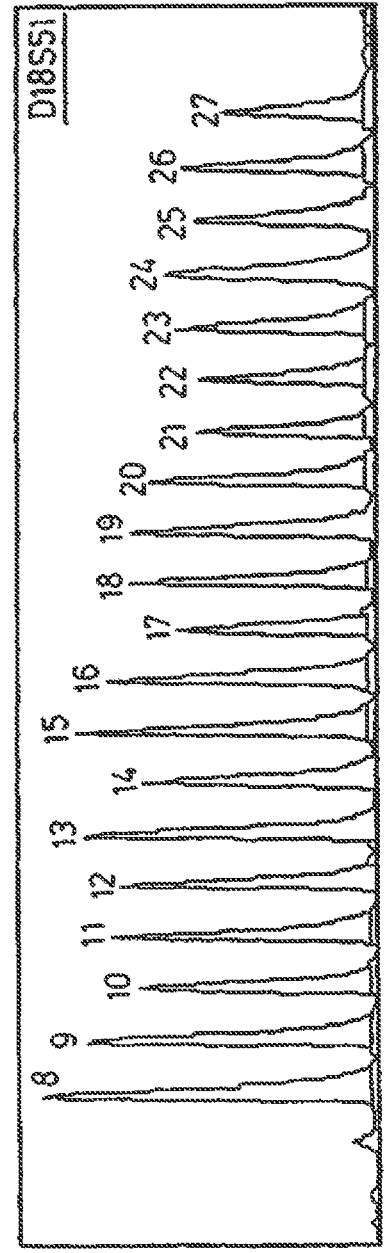
FIG. 2g shows an electrophoretogram of the allelic ladder for D18551.

Electrophoretograms for the allelic ladders are shown in FIGS. 2a to 2g with the allelic number designations shown.

FIGS. 3a to 3f show the sequences for the alleles identified in FIGS. 2a to 2g.

The allelic ladder mixture discussed above was produced according to the following techniques. Buccal swabs and/or bloodstains were used as the sample sources. The genomic DNA was extracted using the chelex procedure described by Walsh et al. 1991 Bio. Techniques 1 91-98.

The recovered DNA was quantified by dot hybridisation using a higher primate specific probe, as disclosed in Walsh et al. 1992 Nucleic Acids Res. 20 5061-5065.

Each sample was then amplified according to the conditions set out below in Table 1 with unlabelled oligonucleotide primers, the sequences for which are disclosed in Urquhart et al. 1995 Bio Techniques 18 116-121 and Oldroyd et al. 1995 Electrophoresis 16 334-337.

TABLE 1

| D18 | 95° C. for 60 seconds | D1 | 94° C. for 30 seconds |
|---|---|---|---|
|  | 60° C. for 60 seconds |  | 58° C. for 60 seconds |
|  | 72° C. for 60 seconds |  | 72° C. for 30 seconds |
|  | Method: 28 CYCLES + 72° C. for 10 minutes then hold at 4° C. |  | Method: 26 cycles + 72° C. for 10 minutes then hold at 4° C. |
| D8 | 94° C. for 30 seconds | TH01 | 94° C. for 45 seconds |
|  | 60° C. for 60 seconds | and | 60° C. for 60 seconds |
|  | 72° C. for 60 seconds | VWA | 72° C. for 60 seconds |
|  | Method: 30 cycles + 72° C. for 10 minutes then hold at 4° C. |  | Method: 28 cycles + 72° C. for 10 minutes then hold at 4° C. |
| FGA | 93° C. for 60 seconds | Amelo | 93° C. for 30 seconds |
|  | 60° C. for 60 seconds |  | 58° C. for 75 seconds |
|  | 72° C. for 60 seconds |  | 72° C. for 15 seconds |
|  | Method: 30 cycles + 72° C. for 10 minutes then hold at 4° C. |  | Method: 30 cycles + 72° C. for 10 minutes then hold at 4° C. |

Individual alleles were then isolated and sequence analysis was carried out according to the methods of Barber et al. 1996 Int. Journal Leg. Med. 108 180-185 and Barber and Parkin 1996 Int. Journal. Leg. Med. 109 62-65. Both DNA strands of each allele reported were sequenced and the sequences provided in FIGS. 3a to 3g are the consensus (7 results for this.

The illustrations of the alleles provided in FIGS. 3a to 3g follow the nomenclature recommended by the DNA commission of the International Society of Forensic Haemogenetics 1994 lot. Journal Leg. Med. 107 159-160 where the complete number of tandem repeats observed are designated by the digit. The longhand version of these sequences is provided at the end of the specific description.

To prepare the ladder cocktail amplification of the alleles is necessary. This process was performed by amplifying the purified single alleles described above using a labelled primer in each case. For the locus HUMFIBRA/FGA the ladder was produced from two separate mixes, discussed in more detail below. The primers used are disclosed in Urquhart et al. 1995 Bio Techniques 18 116-121 and Oldroyd et al. 1995 Electrophoresis 16 334-337 and were employed according to the conditions set out above in Table 1.

The singleplexs produced in this way were analysed on an Applied Biosystems 377 automated sequencer to confirm the sequences. The sequences obtained from the profiling system are one base longer than those determined form the DNA sequencing technique initially discussed above. This is due to the ability of DNA polymerase from *Thermus aquaticus* to catalyse a non-template mediated addition of a deoxyribonucleotide to the 3' hydroxyl of PCR products. This is generally known as the "n+1" product and can be generated in preference to the "n" product. The results reported here, however, refer to the "n" product rather than the "n+1" product for which the labelled primer PCR conditions have been optimised to produce.

The products of the amplification process for each locus were then diluted, mixed with one another and reanalysed to produce a single ladder for each loci having even peak heights. An initial level of 1000 Arbitary Units, AU, was increased to 1000-5000 AU to give greater signal strength and volume for the ladder.

The single ladders produced in this way were then mixed together to give the cocktail discussed above. The proportions of each ladder used are controlled to give balanced peak areas. The cocktail was then validated using Applied Biosystems 373A and Applied Biosystems 377 automated sequencers with Genescan and Genotyper software.

Allelic ladders according to the invention can be prepared by applying PCR amplification techniques to a pre-existing sample of the allelic ladder mixture. Alternatively the allelic ladders can be constructed from the sequence information provided herein.

The new ladders disclosed above significantly extends the range of alleles which can be identified in any DNA profiling system.

The allelic ladder mixture is used as a control sample alongside samples from known or unknown individuals which are then segregated according to size in a gel. Alleles in the sample under test can be designated by the known alleles in the control if they are within 0.5 bases of one another. Alleles falling outside this range are estimated based on their position relative to the ladder.

Using the standard nomenclature discussed above, the ladder range for each locus, defined by the extreme low molecular weight and extreme high molecular weight alleles are:

| Locus | Low MW allele | High MW allele |
|---|---|---|
| a) HUMVWFA31/A | 10 | 21 |
| b) HUMTH01 | 4 | 13.3 |
| c) D8S1179 | 7 | 19 |
| d) HUMFIBRA/FGA | 16.1 | 50.2 |
| e) D21S11 | 53 | 81 |
| f) D18S51 | 8 | 27 |

The allelic ladders also enable the identification of certain rare and hence highly discriminatory alleles in DNA profiling, thus increasing the profiling systems power.

For the various locus certain alleles are of particular significance as follows:

Locus HUMTHO1

The primers used for this locus were labelled with 6-FAM. The polymorphic region of this locus is based around a tetranucleotide motif repeat, $(TCAT)_n$, where n=4 to 13. Particular alleles provided by the present invention include 4, 9.3, 10 and 13.3. The 9.3 and 13.3 alleles were found to have a deletion of a thiamine nucleotide at either the last base of the 4th repeat unit or the first base of the 5th repeat unit. The 13.3 allele notably possesses a non-consensus tetranucleotide (TCGT) at the 13th repeat, Locus D21S11

The primers for this locus were also labeled with 6-FAM. The allele range extends from 53 to 81 and significantly includes alleles 53, 56, 57, 79 and 81. The polymorphic region of the D21S11 alleles is relatively complex in structure and is based around the tetranucleotide TCTR, where R is A or G (following the ambiguity codes of the Nomenclature Committee of the International Union of Biochemistry), as well as containing invariant hexa-, tri- and di-nucleotides. Both allele 54 and allele 56 deviate from this general structure in that they possess a deletion of a 14 base pair TA(TCTA)$_3$ (SEQ ID NO: 37) unit immediately prior to the invariant TCA tetranucleotide.

Locus D18S51

Again primers with a 6-FAM label were used. The ladder extends to 20 distinct alleles with particularly significant alleles at 8, 9, 23, 24, 45, 26 and 27. The polymorphic region is based around a simple tetranucleotide repeat motif (AGAA), (SEQ ID NO: 38), where n is 8 to 27.

Locus D8S1179

The primers used for this locus were labeled with TET. The ladder extends from alleles 7 to 19, based on 13 separate alleles. Significant alleles include 7, 15, 18 and 19. A Different generalized structures were observed between the upper and lower molecular weight ends of the ladder. In the lower molecular weight area, 161 to 177 base pairs, a simple repeat region based on the tetranucleotide TCTA exists. In the higher weight region, 181 to 201 base pairs, a compound repeat region composed of the tetranucleotide TCTR was found.

Locus HUMVWFA31/A

HEX labeled primers were used for this locus. The ladder covers alleles between 10 and 21, based on 12 alleles in total. Noteworthy alleles 10, 11 and 12 are included. The polymorphic unit is generally composed of a compound repeat following the pattern (TCTR)n. For the 13 and 14 alleles a non-consensus TCCA tetranucleotide at the 10th and 11th repeats was found.

Locus HUMFIBRA/FGA

This locus also employed HEX labelled primers. As mentioned above this ladder was constructed in two separate components. A low molecular weight and high molecular weight mix was used to produce the overall ladder. The low molecular weight mix ranges from allele 16.1 to 34.2 and the high molecular weight mix from allele 42.2 to 50.2.

The low MW mix includes significant alleles 16.1, 28, 30, 30.2, 31.2, 32.2, 33.2 and 34.2. The high MW mix includes noteworthy alleles 42.2, 43.2, 44.2, 45.2, 47.2, 48.2 and 50.2.

In general the HUMFIBRA/FGA alleles have a polymorphic unit based around the compound repeat YYBY, with the alleles in the upper part of the weight range being more complex in structure than those in the lower part. Within the general framework, allele 16.1 has a T nucleotide addition in the repeat region and allele 27 has a C to T transition in the 19th repeat unit (CTTT to CCTT). The upper MW allele range includes a stutter peak which is 4 base pairs smaller than the 50.2 allele. This artifact corresponds to allele 49.2 which has not currently been determined.

Amelogenin

Primers for this locus were once again labeled with 6-FAM. The sequence data revealed an X specific product of 105 base pairs and a Y specific product of 111 base pairs.

```
HUMTH01 Allele Sequences
                                                                (SEQ ID NO: 4)
13.3  (TCAT)4 CAT (TCAT)7 TCAT D21S11 Alleles Sequences
                                                                (SEQ ID NO: 19)
53    (TCTA)4  (TCTG)6  (TCTA)3  TA(TCTA)3 TCA  (TCTA)2  TCCATA  (TCTA)6  TCGTCT (SEQ ID NO: 20)
54    (TCTA)5  (TCTG)6  (TCTA)3  TCA  (TCTA)2  TCCATA  (TCTA)9  TCGTCT (SEQ ID NO: 21)
56    (TCTA)5  (TCTG)6  (TCTA)3  TCA  (TCTA)2  TCCATA  (TCTA)10 TCGTCT (SEQ ID NO: 22)
57    (TCTA)4  (TCTG)6  (TCTA)3  TA  (TCTA)3  TCA  (TCTA)2  TCCATA  (TCTA)8  TCGTCT (SEQ ID NO: 23)
59    (TCTA)5  (TCTG)5  (TCTA)3  TA  (TCTA)3  TCA  (TCTA)2  TCCATA  (TCTA)9  TCGTCT (SEQ ID NO: 24)
61    (TCTA)4  (TCTG)6  (TCTA)3  TA  (TCTA)3  TCA  (TCTA)2  TCCATA  (TCTA)10 TCGTCT (SEQ ID NO: 25)
63    (TCTA)4  (TCTG)6  (TCTA)3  TA  (TCTA)3  TCA  (TCTA)2  TCCATA  (TCTA)11 TCGTCT (SEQ ID NO: 26)
65    (TCTA)6  (TCTG)5  (TCTA)3  TA  (TCTA)3  TCA  (TCTA)2  TCCATA  (TCTA)11 TCGTCT (SEQ ID NO: 27)
67    (TCTA)5  (TCTG)6  (TCTA)3  TA  (TCTA)3  TCA  (TCTA)2  TCCATA  (TCTA)12 TCGTCT (SEQ ID NO: 28)
68    (TCTA)5  (TCTG)6  (TCTA)3  TA  (TCTA)3  TCA  (TCTA)2  TCCATA  (TCTA)11 TATCTA
      TCGTCT (SEQ ID NO: 29)
70    (TCTA)5  (TCTG)6  (TCTA)3  TA  (TCTA)3  TCA  (TCTA)2  TCCATA  (TCTA)12 TATCTA
      TCGTCT (SEQ ID NO: 30)
72    (TCTA)5  (TCTG)6  (TCTA)3  TA  (TCTA)3  TCA  (TCTA)2  TCCATA  (TCTA)13 TATCTA
      TCGTCT
```

-continued

```
                                                           (SEQ ID NO: 31)
74  (TCTA)5 (TCTG)6 (TCTA)3 TA (TCTA)3 TCA (TCTA)2 TCCATA (TCTA)14 TATCTA
    TCGTCT (SEQ ID NO: 32)
75  (TCTA)10 (TCTG)5 (TCTA)3 TA (TCTA)3 TCA (TCTA)2 TCCATA (TCTA)12 TCGTCT (SEQ ID NO: 33)
77  (TCTA)11 (TCTG)5 (TCTA)3 TA (TCTA)3 TCA (TCTA)2 TCCATA (TCTA)12 TCGTCT (SEQ ID NO: 34)
79  (TCTA)11 (TCTG)5 (TCTA)3 TA (TCTA)3 TCA (TCTA)2 TCCATA (TCTA)13 TCGTCT (SEQ ID NO: 35)
81  (TCTA)13 (TCTG)5 (TCTA)3 TA (TCTA)3 TCA (TCTA)2 TCCATA (TCTA)12 TCGTCT

D18S51 Allele Sequences
                                                           (SEQ ID NO: 36)
 8  (AGAA)8

D8S1179 Allele Sequences
                                                           (SEQ ID NO: 5)
 7  (TCTA)8

(SEQ ID NO: 6)
19  (TCTA)2 TCTG (TCTA)16

HUMVWAF31/A Allele Sequences
                                                           (SEQ ID NO: 1)
10  TCTA TCTG TCTA (TCTG)4 (TCTA)3

(SEQ ID NO: 2)
12  TCTA (TCTG)4 (TCTA)7

(SEQ ID NO: 3)
13  (TCTA)2 (TCTG)4 (TCTA)3 TCCA (TCTA)3
```

(Note also that the allele has an atypical 3' flanking sequence. The usual sequence is TCCA TCTA T. In this allele the sequence is (TCCA)2T.

```
HUMFIBRA(FGA) Allele Sequences
                                                           (SEQ ID NO: 7)
16.1 (TTTC)3 TTTT TTCT (CTTT)5 T (CTTT)3 CTCC (TTCC)2

(SEQ ID NO: 8)
27   (TTTC)3 TTTT TTCT (CTTT)13 CCTT (CTTT)5 CTCC (TTCC)2

(SEQ ID NO: 9)
30   (TTTC)3 TTTT TTCT (CTTT)16 CCTT (CTTT)5 CTCC (TTCC)2

(SEQ ID NO: 10)
31.2 (TTTC)4 TTTT TT (CTTT)15 (CTTC)3 (CTTT)3 CTCC (TTCC)4

(SEQ ID NO: 11)
32.2 (TTTC)4 TTTT TT (CTTT)16 (CTTC)3 (CTTT)3 CTCC (TTCC)4

(SEQ ID NO: 12)
33.2 (TTTC)4 TTTT TT (CTTT)17 (CTTC)3 (CTTT)3 CTCC (TTCC)4

(SEQ ID NO: 13)
42.2 (TTTC)4 TTTT TT (CTTT)8 (CTGT)4 (CTTT)13 (CTTC)4 (CTTT)3 CTCC (TTCC)4

(SEQ ID NO: 14)
43.2 (TTTC)4 TTTT TT (CTTT)8 (CTGT)5 (CTTT)13 (CTTC)4 (CTTT)3 CTCC (TTCC)4

(SEQ ID NO: 15)
44.2 (TTTC)4 TTTT TT (CTTT)11 (CTGT)3 (CTTT)14 (CTTC)3 (CTTT)3 CTCC (TTCC)4

(SEQ ID NO: 16)
45.2 (TTTC)4 TTTT TT (CTTT)10 (CTGT)5 (CTTT)13 (CTTC)4 (CTTT)3 CTCC (TTCC)4

(SEQ ID NO: 17)
47.2 (TTTC)4 TTTT TT (CTTT)12 (CTGT)5 (CTTT)14 (CTTC)3 (CTTT)3 CTCC (TTCC)4

(SEQ ID NO: 18)
48.2 (TTTC)4 TTTT TT (CTTT)14 (CTGT)3 (CTTT)14 (CTTC)4 (CTTT)3 CTCC (TTCC)4
```

(1) GENERAL INFORMATION:

```
(i)  APPLICANT:
     (A) NAME: Griffiths, Rebecca A. L.
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Barber, Michael D.
     (B) STREET: c/o The Forensic Science Service, Priory House, Gooch St.
     (C) CITY: Birmingham
     (D) STATE.: W Midlands
     (E) COUNTRY: United Kingdom
     (F) POSTAL CODE (ZIP): B5 6QQ (A) NAME: Johnson, Peter E.
     (B) STREET: c/o The Forensic Science Service, Priory House, Gooch St.
     (C) CITY: Birmingham
     (D) STATE: W Midlands
     (F) COUNTRY: United Kingdom
     (F) POSTAL CODE (ZIP): B5 6QQ (A) NAME: Gillbard, Sharon M.
     (B) STREET: c/o The Forensic Science Service, Priory House, Gooch St.
     (C) CITY; Birmingham
     (D) STATE: W Midlands
     (E) COUNTRY: United Kingdom
     (F) POSTAL CODE (ZIP): B5 6QQ (A) NAME: Haywood, Marc D.
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Smith, Carolyn D.
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Arnold, Jennifer
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Burke, Trudy
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Urquhart, Andrew J.
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (A) NAME: Gill, Peter
     (B) STREET: c/o The Forensic Science Service, Priory House, Gooch St.
     (C) CITY: Birmingham
     (D) STATE: W Midlands
     (E) COUNTRY: United Kingdom
     (F) POSTAL CODE (ZIP): B5 6QQ (ii) TITLE OF INVENTION: Improvements in and relating to forensic identification (iii)NUMBER OF SEQUENCES: 36
```

```
   (iv) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.30 (EPO)

(vi) PRIOR APPLICATION DATA:
        (A) APPLICATION NUMBER: GB 9713597.4
        (B) FILING DATE: 28 Jun. 1997

(2) INFORMATION FOR SEQ ID NO: 1:

(i)  SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii)HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 1:

TCTATCTGTC TATCTGTCTG TCTGTCTGTC TATCTATCTA (2) INFORMATION FOR SEQ ID NO: 2:

(i)  SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii)HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 2:

TCTATCTGTC TGTCTGTCTG TCTATCTATC TATCTATCTA TCTATCTA (2) INFORMATION FOR SEQ ID NO: 3:

(i)  SEQUENCE CHARACTERISTICS:
        (A) LENGTH: 52 base pairs
        (B) TYPE: nucleic acid.
        (C) STRANDEDNESS: single
        (D) TOPOLOGY: linear (ii) MOLECULE TYPE: DNA (genomic)

(iii)HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 3:

TCTATCTATC TGTCTGTCTG TCTGTCTATC TATCTATCCA TCTATCTATC TA (2) INFORMATION FOR SEQ ID NO: 4:

(i)  SEQUENCE CHARACTERISTICS:
        (A) LENGTH: 55 base pairs
        (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens
         (I) ORGANELLE: Mitochondrion (xi) SEQUENCE DESCRIPTION: SEQ ID NO: 4:

TCATTCATTC ATTCATCATT CATTCATTCA TTCATTCATT CATTCATTCG TTCAT (2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens
         (I) ORGANELLE: Mitochondrion (xi) SEQUENCE DESCRIPTION: SEQ ID NO: 5:

TCTATCTATC TATCTATCTA TCTATCTATC TA (2) INFORMATION FOR SEQ ID NO: 6:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens
         (I) ORGANELLE: Mitochondrion (xi) SEQUENCE DESCRIPTION: SEQ ID NO: 6:

TCTATCTATC TGTCTATCTA TCTATCTATC TATCTATCTA TCTATCTATC

TATCTATCTA

TCTATCTATC TATCTA (2) INFORMATION FOR SEQ ID NO: 7:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

```
        (vi) ORIGINAL SOURCE:
             (A) ORGANISM: Homo sapiens
             (I) ORGANELLE: Mitochondrion (xi) SEQUENCE DESCRIPTION: SEQ ID NO: 7:

TTTCTTTCTT TCTTTTTTCT CTTTCTTTCT TTCTTTCTTT TCTTTCTTTC TTTCTCCTTC

CTTCC (2) INFORMATION FOR SEQ ID NO: 8:

(i)  SEQUENCE CHARACTERISTICS:
             (A) LENGTH: 108 base pairs
             (B) TYPE: nucleic acid
             (C) STRANDEDNESS: single
             (D) TOPOLOGY: linear (ii) MOLECULE TYPE: DNA (genomic)

(iii)HYPOTHETICAL: NO (iv) ANTI-SENSE: NO (vi) ORIGINAL SOURCE:
             (A) ORGANISM: Homo sapiens
             (I) ORGANELLE: Mitochondrion (xi) SEQUENCE DESCRIPTION: SEQ ID NO: 8:

TTTCTTTCTT TCTTTTTTCT CTTTCTTTCT TTCTTTCTTT CTTTCTTTCT

TTCTTTCTTT

CTTTCTTTCT TTCCTTCTTT CTTTCTTTCT TTCTTTCTCC TTCCTTCC (2) INFORMATION FOR SEQ ID NO: 9:

(i)  SEQUENCE CHARACTERISTICS:
             (A) LENGTH: 120 base pairs
             (B) TYPE: nucleic acid
             (C) STRANDEDNESS: single
             (D) TOPOLOGY: linear (ii) MOLECULE TYPE: DNA (genomic)

(iii)HYPOTHETICAL: NO (iv) ANTI-SENSE: NO (vi) ORIGINAL SOURCE:
             (A) ORGANISM: Homo sapiens
             (I) ORGANELLE: Mitochondrion (xi) SEQUENCE DESCRIPTION: SEQ ID NO: 9:

TTTCTTTCTT TCTTTTTTCT CTTTCTTTCT TTCTTTCTTT CTTTCTTTCT

TTCTTTCTTT

CTTTCTTTCT TTCTTTCTTT CTTCCTTCT TTCTTTCTTT CTTTCTTTCT

CCTTCCTTCC (2) INFORMATION FOR SEQ ID NO: 10:

(i)  SEQUENCE CHARACTERISTICS:
             (A) LENGTH: 126 base pairs
             (B) TYPE: nucleic acid
             (C) STRANDEDNESS: single
             (D) TOPOLOGY: linear (ii) MOLECULE TYPE: DNA (genomic)

(iii)HYPOTHETICAL: NO (iv) ANTI-SENSE: NO
```

(vi) ORIGINAL SOURCE:
            (A) ORGANISM: *Homo sapiens*
            (I) ORGANELLE: Mitochondrion (xi) SEQUENCE DESCRIPTION: SEQ ID NO: 10:

TTTCTTTCTT TCTTTCTTTT TTCTTTCTTT CTTTCTTTCT TTCTTTCTTT

CTTTCTTTCT

TTCTTTCTTT CTTTCTTTCT TTCTTCCTTC CTTCCTTTCT TTCTTTCTCC

TTCCTTCCTT

CCTTCC (2) INFORMATION FOR SEQ ID NO: 11:

(i)  SEQUENCE CHARACTERISTICS:
            (A) LENGTH: 130 base pairs
            (B) TYPE: nucleic acid
            (C) STRANDEDNESS: single
            (D) TOPOLOGY: linear (ii) MOLECULE TYPE: DNA (genomic)

(iii)HYPOTHETICAL: NO (iv) ANTI-SENSE: NO (vi) ORIGINAL SOURCE:
            (A) ORGANISM: *Homo sapiens*
            (I) ORGANELLE: Mitochondrion (xi) SEQUENCE DESCRIPTION: SEQ ID NO: 11:

TTTCTTTCTT TCTTTCTTTT TTCTTTCTTT CTTTCTTTCT TTCTTTCTTT

CTTTCTTTCT

TTCTTTCTTT CTTTCTTTCT TTCTTTCTTC CTTCCTTCCT TTCTTTCTTT

CTCCTTCCTT

CCTTCCTTCC (2) INFORMATION FOR SEQ ID NO: 12:

(i)  SEQUENCE CHARACTERISTICS:
            (A) LENGTH: 134 base pairs
            (B) TYPE: nucleic acid
            (C) STRANDEDNESS: single
            (D) TOPOLOGY: linear (ii) MOLECULE TYPE: DNA (genomic)

(iii)HYPOTHETICAL: NO (iv) ANTI-SENSE: NO (vi) ORIGINAL SOURCE:
            (A) ORGANISM: *Homo sapiens*
            (I) ORGANELLE: Mitochondrion (xi) SEQUENCE DESCRIPTION: SEQ ID NO: 12:

TTTCTTTCTT TCTTTCTTTT TTCTTTCTTT CTTTCTTTCT TTCTTTCTTT

CTTTCTTTCT

TTCTTTCTTT CTTTCTTTCT TTCTTTCTTT CTTCCTTCCT TCCTTTCTTT

CTTTCTCCTT

CCTTCCTTCC TTCC (2) INFORMATION FOR SEQ ID NO: 13:

(i)   SEQUENCE CHARACTERISTICS:
        (A) LENGTH: 170 base pairs
        (B) TYPE: nucleic acid
        (C) STRANDEDNESS: single
        (D) TOPOLOGY: linear (ii)  MOLECULE TYPE: DNA (genomic)

(iii) HYPOTHETICAL: NO (iv)  ANTI-SENSE: NO (vi)  ORIGINAL SOURCE:
        (A) ORGANISM: *Homo sapiens*
        (I) ORGANELLE: Mitochondrion (xi)  SEQUENCE DESCRIPTION: SEQ ID NO: 13:

TTTCTTTCTT TCTTTCTTTT TTCTTTCTTT CTTTCTTTCT TTCTTTCTTT

CTTTCTGTCT

GTCTGTCTGT CTTTCTTTCT TTCTTTCTTT CTTTCTTTCT TTCTTTCTTT

CTTTCTTTCT

TTCTTCCTTC CTTCCTTCCT TTCTTTCTTT CTCCTTCCTT CCTTCCTTCC (2) INFORMATION FOR SEQ ID NO: 14:

(i)   SEQUENCE CHARACTERISTICS:
        (A) LENGTH: 174 base pairs
        (B) TYPE: nucleic acid
        (C) STRANDEDNESS: single
        (D) TOPOLOGY: linear (ii)  MOLECULE TYPE: DNA (genomic)

(iii) HYPOTHETICAL: NO (iv)  ANTI-SENSE: NO (vi)  ORIGINAL SOURCE:
        (A) ORGANISM: *Homo sapiens*
        (I) ORGANELLE: Mitochondrion (xi)  SEQUENCE DESCRIPTION: SEQ ID NO: 14:

TTTCTTTCTT TCTTTCTTTT TTCTTTCTTT CTTTCTTTCT TTCTTTCTTT

CTTTCTGTCT

GTCTGTCTGT CTGTCTTTCT TTCTTTCTTT CTTTCTTTCT TTCTTTCTTT

CTTTCTTTCT

TTCTTTCTTC CTTCCTTCCT TCCTTTCTTT CTTTCTCCTT CCTTCCTTCC TTCC (2) INFORMATION FOR SEQ ID NO: 15:

(i)   SEQUENCE CHARACTERISTICS:
        (A) LENGTH: 178 base pairs
        (B) TYPE: nucleic acid
        (C) STRANDEDNESS: single
        (D) TOPOLOGY: linear (ii)  MOLECULE TYPE: DNA (genomic)

(iii) HYPOTHETICAL: NO (iv)  ANTI-SENSE: NO (vi)  ORIGINAL SOURCE:
        (A) ORGANISM: *Homo sapiens*
        (I) ORGANELLE: Mitochondrion -continued
(xi) SEQUENCE DESCRIPTION: SEQ ID NO: 15:

TTTCTTTCTT TCTTTCTTTT TTCTTTCTTT CTTTCTTTCT TTCTTTCTTT

CTTTCTTTCT

TTCTTTCTGT CTGTCTGTCT TTCTTTCTTT CTTTCTTTCT TTCTTTCTTT

CTTTCTTTCT

TTCTTTCTTT CTTTCTTCCT TCCTTCCTTT CTTTCTTTCT CCTTCCTTCC

TTCCTTCC (2) INFORMATION FOR SEQ ID NO: 16:

(i)  SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(iii)HYPOTHETICAL: NO (iv) ANTI-SENSE: NO (vi) ORIGINAL SOURCE:
        (A) ORGANISM: *Homo sapiens*
        (I) ORGANELLE: Mitochondrion (xi) SEQUENCE DESCRIPTION: SEQ ID NO: 16:

TTTCTTTCTT TCTTTCTTTT TTCTTTCTTT CTTTCTTTCT TTCTTTCTTT

CTTTCTTTCT

TTCTGTCTGT CTGTCTGTCT GTCTTTCTTT CTTTCTTTCT TTCTTTCTTT

CTTTCTTTCT

TTCTTTCTTT CTTTCTTCCT TCCTTCCTTC CTTTCTTTCT TTCTCCTTCC

TTCCTTCCTT

CC (2) INFORMATION FOR SEQ ID NO: 17:

(i)  SEQUENCE CHARACTERISTICS:
        (A) LENGTH: 190 base pairs
        (B) TYPE: nucleic acid
        (C) STRANDEDNESS: single
        (D) TOPOLOGY: linear (ii) MOLECULE TYPE: DNA (genomic)

(iii)HYPOTHETICAL: NO (iv) ANTI-SENSE: NO (vi) ORIGINAL SOURCE:
        (A) ORGANISM: *Homo sapiens*
        (I) ORGANELLE: Mitochondrion (xi) SEQUENCE DESCRIPTION: SEQ ID NO: 17:

TTTCTTTCTT TCTTTCTTTT TTCTTTCTTT CTTTCTTTCT TTCTTTCTTT

CTTTCTTTCT

TTCTTTCTTT CTGTCTGTCT GTCTGTCTGT CTTTCTTTCT TTCTTTCTTT

CTTTCTTTCT

TTCTTTCTTT CTTTCTTTCT TTCTTTCTTC CTTCCTTCCT TTCTTTCTTT

CTCCTTCCTT

CCTTCCTTCC (2) INFORMATION FOR SEQ ID NO: 18:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE
        (A) ORGANISM: *Homo sapiens*
        (I) ORGANELLE: Mitochondrion (xi) SEQUENCE DESCRIPTION: SEQ ID NO: 18:

TTTCTTTCTT TCTTTCTTTT TTCTTTCTTT CTTTCTTTCT TTCTTTCTTT

CTTTCTTTCT

TTCTTTCTTT CTTTCTTTCT GTCTGTCTGT CTTTCTTTCT TTCTTTCTTT

CTTTCTTTCT

TTCTTTCTTT CTTTCTTTCT TTCTTTCTTC CTTCCTTCCT TCCTTTCTTT

CTTTCTCCTT

CCTTCCTTCC TTCC (2) INFORMATION FOR SEQ ID NO: 19:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: *Homo sapiens*
        (I) ORGANELLE: Mitochondrion (xi) SEQUENCE DESCRIPTION: SEQ ID NO: 19:

TCTATCTATC TATCTATCTG TCTGTCTGTC TGTCTGTCTG TCTATCTATC

TATATCTATC

TATCTATCAT CTATCTATCC ATATCTATCT ATCTATCTAT CTATCTATCG TCT (2) INFORMATION FOR SEQ ID NO: 20:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: *Homo sapiens*
        (I) ORGANELLE: Mitochondrion -continued (xi) SEQUENCE DESCRIPTION: SEQ ID NO: 20:

TCTATCTATC TATCTATCTA TCTGTCTGTC TGTCTGTCTG TCTGTCTATC

TATCTATCAT

CTATCTATCC ATATCTATCT ATCTATCTAT CTATCTATCT ATCTATCTAT CGTCT (2) INFORMATION FOR SEQ ID NO: 21:

(i)  SEQUENCE CHARACTERISTICS:
         (A) LENGTH: 119 base pairs
         (B) TYPE: nucleic acid
         (C) STRANDEDNESS: single
         (D) TOPOLOGY: linear (ii) MOLECULE TYPE: DNA (genomic)

(iii)HYPOTHETICAL: NO (iv) ANTI-SENSE: NO (vi) ORIGINAL SOURCE:
         (A) ORGANISM: *Homo sapiens*
         (I) ORGANELLE: Mitochondrion (xi) SEQUENCE DESCRIPTION: SEQ ID NO: 21:

TCTATCTATC TATCTATCTA TCTGTCTGTC TGTCTGTCTG TCTGTCTATC

TATCTATCAT

CTATCTATCC ATATCTATCT ATCTATCTAT CTATCTATCT ATCTATCTAT

CTATCGTCT (2) INFORMATION FOR SEQ ID NO: 22:

(i)  SEQUENCE CHARACTERISTICS:
         (A) LENGTH: 121 base pairs
         (B) TYPE: nucleic acid
         (C) STRANDEDNESS: single
         (D) TOPOLOGY: linear (ii) MOLECULE TYPE: DNA (genomic)

(iii)HYPOTHETICAL: NO (iv) ANTI-SENSE: NO (vi) ORIGINAL SOURCE:
         (A) ORGANISM: *Homo sapiens*
         (I) ORGANELLE: Mitochondrion (xi) SEQUENCE DESCRIPTION: SEQ ID NO: 22:

TCTATCTATC TATCTATCTG TCTGTCTGTC TGTCTGTCTG TCTATCTATC

TATATCTATC

TATCTATCAT CTATCTATCC ATATCTATCT ATCTATCTAT CTATCTATCT

ATCTATCGTC

T (2) INFORMATION FOR SEQ ID NO: 23:

(i)  SEQUENCE CHARACTERISTICS:
         (A) LENGTH: 125 base pairs
         (B) TYPE; nucleic acid
         (C) STRANDEDNESS: single
         (D) TOPOLOGY: linear (ii) MOLECULE TYPE: DNA (genomic)

(iii)HYPOTHETICAL: NO (iv) ANTI-SENSE: NO

```
    (vi) ORIGINAL SOURCE:
         (A) ORGANISM: Homo sapiens
         (I) ORGANELLE: Mitochondrion (xi) SEQUENCE DESCRIPTION: SEQ ID NO: 23:

TCTATCTATC TATCTATCTA TCTGTCTGTC TGTCTGTCTG TCTATCTATC

TATATCTATC

TATCTATCAT CTATCTATCC ATATCTATCT ATCTATCTAT CTATCTATCT

ATCTATCTAT

CGTCT (2) INFORMATION FOR SEQ ID NO: 24:

(i) SEQUENCE CHARACTERISTICS:
         (A) LENGTH: 129 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens
         (I) ORGANELLE: Mitochondrion (xi) SEQUENCE DESCRIPTION: SEQ ID NO: 24:

TCTATCTATC TATCTATCTG TCTGTCTGTC TGTCTGTCTG TCTATCTATC

TATATCTATC

TATCTATCAT CTATCTATCC ATATCTATCT ATCTATCTAT CTATCTATCT

ATCTATCTAT

CTATCGTCT (2) INFORMATION FOR SEQ ID NO: 25:

(i) SEQUENCE CHARACTERISTICS:
         (A) LENGTH: 133 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens
         (I) ORGANELLE: Mitochondrion (xi) SEQUENCE DESCRIPTION: SEQ ID NO: 25:

TCTATCTATC TATCTATCTG TCTGTCTGTC TGTCTGTCTG TCTATCTATC

TATATCTATC

TATCTATCAT CTATCTATCC ATATCTATCT ATCTATCTAT CTATCTATCT

ATCTATCTAT

CTATCTATCG TCT (2) INFORMATION FOR SEQ ID NO: 26:

(i) SEQUENCE CHARACTERISTICS:
         (A) LENGTH: 137 base pairs
         (B) TYPE: nucleic acid
```

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 26:

TCTATCTATC TATCTATCTA TCTATCGTC TGTCTCTCTG TCTGTCTATC

TATCTATATC

TATCTATCTA TCATCTATCT ATCCATATCT ATCTATCTAT CTATCTATCT

ATCTATCTAT

CTATCTATCT ATCGTCT (2) INFORMATION FOR SEQ ID NO: 27:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 27:

TCTATCTATC TATCTATCTA TCTGTCTGTC TGTCTGTCTG TCTGTCTATC

TATCTATATC

TATCTATCTA TCATCTATCT ATCCATATCT ATCTATCTAT CTATCTATCT

ATCTATCTAT

CTATCTATCT ATCTATCGTC T (2) INFORMATION FOR SEQ ID NO: 28:

(i) SEQUENCE CHARACTERISTICS:
        (A) LENGTH: 143 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 28:

TCTATCTATC TATCTATCTA TCTGTCTGTC TGTCTGTCTG TCTGTCTATC

TATCTATATC

TATCTATCTA TCATCTATCT ATCCATATCT ATCTATCTAT CTATCTATCT
```

```
ATCTATCTAT

CTATCTATCT ATATCTATCG TCT (2) INFORMATION FOR SEQ ID NO: 29:

(i)   SEQUENCE CHARACTERISTICS:
          (A) LENGTH: 147 base pairs
          (B) TYPE: nucleic acid
          (C) STRANDEDNESS: single
          (D) TOPOLOGY: linear (ii)  MOLECULE TYPE: DNA (genomic)

(iii) HYPOTHETICAL: NO (iv)  ANTI-SENSE: NO (vi)  ORIGINAL SOURCE:
          (A) ORGANISM: Homo sapiens
          (I) ORGANELLE: Mitochondrion (xi)  SEQUENCE DESCRIPTION: SEQ ID NO: 29:

TCTATCTATC TATCTATCTA TCTGTCTGTC TGTCTGTCTG TCTGTCTATC

TATCTATATC

TATCTATCTA TCATCTATCT ATCCATATCT ATCTATCTAT CTATCTATCT

ATCTATCTAT

CTATCTATCT ATCTATATCT ATCGTCT (2) INFORMATION FOR SEQ ID NO: 30:

(i)   SEQUENCE CHARACTERISTICS:
          (A) LENGTH: 151 base pairs
          (B) TYPE: nucleic acid
          (C) STRANDEDNESS: single
          (D) TOPOLOGY: linear (ii)  MOLECULE TYPE: DNA (genomic)

(iii) HYPOTHETICAL: NO (iv)  ANTI-SENSE: NO (vi)  ORIGINAL SOURCE:
          (A) ORGANISM: Homo sapiens
          (I) ORGANELLE: Mitochondrion (xi)  SEQUENCE DESCRIPTION: SEQ ID NO: 30:

TCTATCTATC TATCTATCTA TCTGTCTGTC TGTCTGTCTG TCTGTCTATC

TATCTATATC

TATCTATCTA TCATCTATCT ATCCATATCT ATCTATCTAT CTATCTATCT

ATCTATCTAT

CTATCTATCT ATCTATCTAT ATCTATCGTC T (2) INFORMATION FOR SEQ ID NO: 31:

(i)   SEQUENCE CHARACTERISTICS:
          (A) LENGTH: 155 base pairs
          (B) TYPE: nucleic acid
          (C) STRANDEDNESS: single
          (D) TOPOLOGY: linear (ii)  MOLECULE TYPE: DNA (genomic)

(iii) HYPOTHETICAL NO (iv)  ANTI-SENSE: NO (vi)  ORIGINAL SOURCE:
          (A) ORGANISM: Homo sapiens
          (I) ORGANELLE: Mitochondrion
```

(xi) SEQUENCE DESCRIPTION: SEQ ID NO: 31:

TCTATCTATC TATCTATCTA TCTGTCTGTC TGTCTGTCTG TCTGTCTATC

TATCTATATC

TATCTATCTA TCATCTATCT ATCCATATCT ATCTATCTAT CTATCTATCT

ATCTATCTAT

CTATCTATCT ATCTATCTAT CTATATCTAT CGTCT (2) INFORMATION FOR SEQ ID NO: 32:

(i) SEQUENCE CHARACTERISTICS:
            (A) LENGTH: 157 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: *Homo sapiens*
            (I) ORGANELLE: Mitochondrion (xi) SEQUENCE DESCRIPTION: SEQ ID NO: 32:

TCTATCTATC TATCTATCTA TCTATCTATC TATCTATCTA TCTGTCTGTC

TGTCTGTCTG

TCTATCTATC TATATCTATC TATCTATCAT CTATCTATCC ATATCTATCT

ATCTATCTAT

CTATCTATCT ATCTATCTAT CTATCTATCT ATCGTCT (2) INFORMATION FOR SEQ ID NO: 33:

(i) SEQUENCE CHARACTERISTICS:
            (A) LENGTH: 161 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: *Homo sapiens*
            (I) ORGANELLE: Mitochondrion (xi) SEQUENCE DESCRIPTION: SEQ ID NO: 33:

TCTATCTATC TATCTATCTA TCTATCTATC TATCTATCTA TCTATCTGTC

TGTCTGTCTG

TCTGTCTATC TATCTATATC TATCTATCTA TCATCTATCT ATCCATATCT

ATCTATCTAT

CTATCTATCT ATCTATCTAT CTATCTATCT ATCTATCGTC T (2) INFORMATION FOR SEQ ID NO: 34:

(i) SEQUENCE CHARACTERISTICS:
            (A) LENGTH: 165 base pairs
            (B) TYPE: nucleic acid
            (C) STRANDEDNESS: single
            (D) TOPOLOGY: linear

```
   (ii) MOLECULE TYPE: DNA (genomic)

(iii) HYPOTHETICAL NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 34:

TCTATCTATC TATCTATCTA TCTATCTATC TATCTATCTA TCTATCTGTC

TGTCTGTCTG

TCTGTCTATC TATCTATATC TATCTATCTA TCATCTATCT ATCCATATCT

ATCTATCTAT

CTATCTATCT ATCTATCTAT CTATCTATCT ATCTATCTAT CGTCT (2) INFORMATION FOR SEQ ID NO: 35:

(i) SEQUENCE CHARACTERISTICS:
        (A) LENGTH: 169 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 35:

TCTATCTATC TATCTATCTA TCTATCTATC TATCTATCTA TCTATCTATC

TATCTGTCTG

TCTGTCTGTC TGTCTATCTA TCTATATCTA TCTATCTATC ATCTATCTAT

CCATATCTAT

CTATCTATCT ATCTATCTAT CTATCTATCT ATCTATCTAT CTATCGTCT (2) INFORMATION FOR SEQ ID NO: 36:

(I) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (I) ORGANELLE: Mitochondrion (xi) SEQUENCE DESCRIPTION: SEQ ID NO: 36:

AGAAAGAAAG AAAGAAAGAA AGAAAGAAAG AA
```

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

```
                              SEQUENCE LISTING

<160> NUMBER OF SEQ ID NOS: 39

<210> SEQ ID NO 1
<211> LENGTH: 40
<212> TYPE: DNA
<213> ORGANISM: Homo sapiens

<400> SEQUENCE: 1
tctatctgtc tatctgtctg tctgtctgtc tatctatcta                               40

<210> SEQ ID NO 2
<211> LENGTH: 48
<212> TYPE: DNA
<213> ORGANISM: Homo sapiens

<400> SEQUENCE: 2
tctatctgtc tgtctgtctg tctatctatc tatctatcta tctatcta                     48

<210> SEQ ID NO 3
<211> LENGTH: 52
<212> TYPE: DNA
<213> ORGANISM: Homo sapiens

<400> SEQUENCE: 3
tctatctatc tgtctgtctg tctgtctatc tatctatcca tctatctatc ta                52

<210> SEQ ID NO 4
<211> LENGTH: 55
<212> TYPE: DNA
<213> ORGANISM: Homo sapiens

<400> SEQUENCE: 4
tcattcattc attcatcatt cattcattca ttcattcatt cattcattcg ttcat             55

<210> SEQ ID NO 5
<211> LENGTH: 32
<212> TYPE: DNA
<213> ORGANISM: Homo sapiens

<400> SEQUENCE: 5
tctatctatc tatctatcta tctatctatc ta                                      32

<210> SEQ ID NO 6
<211> LENGTH: 76
<212> TYPE: DNA
<213> ORGANISM: Homo sapiens

<400> SEQUENCE: 6
tctatctatc tgtctatcta tctatctatc tatctatcta tctatctatc tatctatcta        60
tctatctatc tatcta                                                        76

<210> SEQ ID NO 7
<211> LENGTH: 65
<212> TYPE: DNA
<213> ORGANISM: Homo sapiens

<400> SEQUENCE: 7
tttctttctt tcttttttct ctttctttct ttctttcttt tctttctttc tttctccttc        60
```

```
cttcc                                                                65

<210> SEQ ID NO 8
<211> LENGTH: 108
<212> TYPE: DNA
<213> ORGANISM: Homo sapiens

<400> SEQUENCE: 8
tttctttctt tctttttttct ctttctttct ttctttcttt ctttctttct ttctttcttt    60
ctttctttct ttccttcttt ctttctttct ttctttctcc ttccttcc                 108

<210> SEQ ID NO 9
<211> LENGTH: 120
<212> TYPE: DNA
<213> ORGANISM: Homo sapiens

<400> SEQUENCE: 9
tttctttctt tctttttttct ctttctttct ttctttcttt ctttctttct ttctttcttt    60
ctttctttct ttctttcttt ctttccttct ttctttcttt ctttctttct ccttccttcc   120

<210> SEQ ID NO 10
<211> LENGTH: 126
<212> TYPE: DNA
<213> ORGANISM: Homo sapiens

<400> SEQUENCE: 10
tttctttctt tctttcttttt ttctttcttt ctttctttct ttctttcttt ctttctttct    60
ttctttcttt ctttctttct ttcttccttc ctttcctttct ttctttctcc ttccttcctt  120
ccttcc                                                               126

<210> SEQ ID NO 11
<211> LENGTH: 130
<212> TYPE: DNA
<213> ORGANISM: Homo sapiens

<400> SEQUENCE: 11
tttctttctt tctttcttttt ttctttcttt ctttctttct ttctttcttt ctttctttct    60
ttctttcttt ctttctttct ttctttcttc cttccttcct ttctttcttt ctccttcctt   120
ccttccttcc                                                           130

<210> SEQ ID NO 12
<211> LENGTH: 134
<212> TYPE: DNA
<213> ORGANISM: Homo sapiens

<400> SEQUENCE: 12
tttctttctt tctttcttttt ttctttcttt ctttctttct ttctttcttt ctttctttct    60
ttctttcttt ctttctttct ttctttcttt ttccttcct tccttcttt ctttctccttc   120 ccttccttcc ttcc                                                      134

<210> SEQ ID NO 13
<211> LENGTH: 170
<212> TYPE: DNA
<213> ORGANISM: Homo sapiens

<400> SEQUENCE: 13
tttctttctt tctttcttttt ttctttcttt ctttctttct ttctttcttt ctttctgtct    60
```

```
gtctgtctgt ctttctttct ttcttctttt ctttctttct ttctttcttt ctttctttct    120
ttcttccttc cttccttcct ttctttcttt ctccttcctt ccttccttcc               170

<210> SEQ ID NO 14
<211> LENGTH: 174
<212> TYPE: DNA
<213> ORGANISM: Homo sapiens

<400> SEQUENCE: 14
tttctttctt tctttctttt ttcttctttt ctttctttct ttctttcttt ctttctgtct    60
gtctgtctgt ctgtctttct ttcttctttt ctttctttct ttctttcttt ctttctttct   120
ttctttcttc cttccttcct tccttctttt ctttctcctt ccttccttcc ttcc          174

<210> SEQ ID NO 15
<211> LENGTH: 178
<212> TYPE: DNA
<213> ORGANISM: Homo sapiens

<400> SEQUENCE: 15
tttctttctt tctttctttt ttcttctttt ctttctttct ttctttcttt ctttctttct    60
ttctttctgt ctgtctgtct ttcttctttt ctttctttct ttctttcttt ctttctttct   120
ttctttcttt ctttcttcct tccttccttt ctttctttct ccttccttcc ttccttcc     178

<210> SEQ ID NO 16
<211> LENGTH: 182
<212> TYPE: DNA
<213> ORGANISM: Homo sapiens

<400> SEQUENCE: 16
tttctttctt tctttctttt ttcttctttt ctttctttct ttctttcttt ctttctttct    60
ttctgtctgt ctgtctgtct gtctttcttt ctttcttctt ctttctttct ttctttctct   120
ttctttcttt ctttcttcct tccttccttc ctttctttct ttctccttcc ttccttcctt   180
cc                                                                   182

<210> SEQ ID NO 17
<211> LENGTH: 190
<212> TYPE: DNA
<213> ORGANISM: Homo sapiens

<400> SEQUENCE: 17
tttctttctt tctttctttt ttcttctttt ctttctttct ttctttcttt ctttctttct    60
ttctttcttt ctgtctgtct gtctgtctgt ctttcttctt ctttctttct ttctttcttt   120
ttctttcttt ctttctttct ttcttctttc cttccttcct ttctttcttt ctccttcctt   180
ccttccttcc                                                           190

<210> SEQ ID NO 18
<211> LENGTH: 194
<212> TYPE: DNA
<213> ORGANISM: Homo sapiens

<400> SEQUENCE: 18
tttctttctt tctttctttt ttcttctttt ctttctttct ttctttcttt ctttctttct    60
ttctttcttt ctttctttct gtctgtctgt ctttcttctt ctttctttct ttctttcttt   120
ttctttcttt ctttctttct ttcttctttc cttccttcct tcctttcttt ctttctcctt   180
ccttccttcc ttcc                                                      194
```

<210> SEQ ID NO 19
<211> LENGTH: 113
<212> TYPE: DNA
<213> ORGANISM: Homo sapiens

<400> SEQUENCE: 19
tctatctatc tatctatctg tctgtctgtc tgtctgtctg tctatctatc tatatctatc      60
tatctatcat ctatctatcc atatctatct atctatctat ctatctatcg tct            113

<210> SEQ ID NO 20
<211> LENGTH: 115
<212> TYPE: DNA
<213> ORGANISM: Homo sapiens

<400> SEQUENCE: 20
tctatctatc tatctatcta tctgtctgtc tgtctgtctg tctgtctatc tatctatcat      60
ctatctatcc atatctatct atctatctat ctatctatct atctatctat cgtct          115

<210> SEQ ID NO 21
<211> LENGTH: 119
<212> TYPE: DNA
<213> ORGANISM: Homo sapiens

<400> SEQUENCE: 21
tctatctatc tatctatcta tctgtctgtc tgtctgtctg tctgtctatc tatctatcat      60
ctatctatcc atatctatct atctatctat ctatctatct atctatctat ctatcgtct      119

<210> SEQ ID NO 22
<211> LENGTH: 121
<212> TYPE: DNA
<213> ORGANISM: Homo sapiens

<400> SEQUENCE: 22
tctatctatc tatctatctg tctgtctgtc tgtctgtctg tctatctatc tatatctatc      60
tatctatcat ctatctatcc atatctatct atctatctat ctatctatct atctatcgtc     120
t                                                                     121

<210> SEQ ID NO 23
<211> LENGTH: 125
<212> TYPE: DNA
<213> ORGANISM: Homo sapiens

<400> SEQUENCE: 23
tctatctatc tatctatcta tctgtctgtc tgtctgtctg tctatctatc tatatctatc      60
tatctatcat ctatctatcc atatctatct atctatctat ctatctatct atctatctat     120
cgtct                                                                 125

<210> SEQ ID NO 24
<211> LENGTH: 129
<212> TYPE: DNA
<213> ORGANISM: Homo sapiens

<400> SEQUENCE: 24
tctatctatc tatctatctg tctgtctgtc tgtctgtctg tctatctatc tatatctatc      60
tatctatcat ctatctatcc atatctatct atctatctat ctatctatct atctatctat     120
ctatcgtct                                                             129

```
<210> SEQ ID NO 25
<211> LENGTH: 133
<212> TYPE: DNA
<213> ORGANISM: Homo sapiens

<400> SEQUENCE: 25
tctatctatc tatctatctg tctgtctgtc tgtctgtctg tctatctatc tatatctatc    60
tatctatcat ctatctatcc atatctatct atctatctat ctatctatct atctatctat   120
ctatctatcg tct                                                       133

<210> SEQ ID NO 26
<211> LENGTH: 137
<212> TYPE: DNA
<213> ORGANISM: Homo sapiens

<400> SEQUENCE: 26
tctatctatc tatctatcta tctatctgtc tgtctgtctg tgtctgtctc tatctatatc    60
tatctatcta tcatctatct atccatatct atctatctat ctatctatct atctatctat   120
ctatctatct atcgtct                                                   137

<210> SEQ ID NO 27
<211> LENGTH: 141
<212> TYPE: DNA
<213> ORGANISM: Homo sapiens

<400> SEQUENCE: 27
tctatctatc tatctatcta tctgtctgtc tgtctgtctg tctgtctatc tatctatatc    60
tatctatcta tcatctatct atccatatct atctatctat ctatctatct atctatctat   120
ctatctatct atctatcgtc t                                              141

<210> SEQ ID NO 28
<211> LENGTH: 143
<212> TYPE: DNA
<213> ORGANISM: Homo sapiens

<400> SEQUENCE: 28
tctatctatc tatctatcta tctgtctgtc tgtctgtctg tctgtctatc tatctatatc    60
tatctatcta tcatctatct atccatatct atctatctat ctatctatct atctatctat   120
ctatctatct atatctatcg tct                                            143

<210> SEQ ID NO 29
<211> LENGTH: 147
<212> TYPE: DNA
<213> ORGANISM: Homo sapiens

<400> SEQUENCE: 29
tctatctatc tatctatcta tctgtctgtc tgtctgtctg tctgtctatc tatctatatc    60
tatctatcta tcatctatct atccatatct atctatctat ctatctatct atctatctat   120
ctatctatct atctatatct atcgtct                                        147

<210> SEQ ID NO 30
<211> LENGTH: 151
<212> TYPE: DNA
<213> ORGANISM: Homo sapiens

<400> SEQUENCE: 30
tctatctatc tatctatcta tctgtctgtc tgtctgtctg tctgtctatc tatctatatc    60
```
tatctatcta tcatctatct atccatatct atctatctat ctatctatct atctatctat    120
ctatctatct atctatctat atctatcgtc t                                    151

<210> SEQ ID NO 31
<211> LENGTH: 155
<212> TYPE: DNA
<213> ORGANISM: Homo sapiens

<400> SEQUENCE: 31
tctatctatc tatctatcta tctgtctgtc tgtctgtctg tctgtctatc tatctatatc     60
tatctatcta tcatctatct atccatatct atctatctat ctatctatct atctatctat    120
ctatctatct atctatctat ctatatctat cgtct                                155

<210> SEQ ID NO 32
<211> LENGTH: 157
<212> TYPE: DNA
<213> ORGANISM: Homo sapiens

<400> SEQUENCE: 32
tctatctatc tatctatcta tctatctatc tatctatcta tctgtctgtc tgtctgtctg     60
tctatctatc tatatctatc tatctatcat ctatctatcc atatctatct atctatctat    120
ctatctatct atctatctat ctatctatct atcgtct                              157

<210> SEQ ID NO 33
<211> LENGTH: 161
<212> TYPE: DNA
<213> ORGANISM: Homo sapiens

<400> SEQUENCE: 33
tctatctatc tatctatcta tctatctatc tatctatcta tctatctgtc tgtctgtctg     60
tctgtctatc tatctatatc tatctatcta tcatctatct atccatatct atctatctat    120
ctatctatct atctatctat ctatctatct atctatcgtc t                         161

<210> SEQ ID NO 34
<211> LENGTH: 165
<212> TYPE: DNA
<213> ORGANISM: Homo sapiens

<400> SEQUENCE: 34
tctatctatc tatctatcta tctatctatc tatctatcta tctatctgtc tgtctgtctg     60
tctgtctatc tatctatatc tatctatcta tcatctatct atccatatct atctatctat    120
ctatctatct atctatctat ctatctatct atctatctat cgtct                     165

<210> SEQ ID NO 35
<211> LENGTH: 169
<212> TYPE: DNA
<213> ORGANISM: Homo sapiens

<400> SEQUENCE: 35
tctatctatc tatctatcta tctatctatc tatctatcta tctatctatc tatctgtctg     60
tctgtctgtc tgtctatcta tctatatcta tctatctatc atctatctat ccatatctat    120
ctatctatct atctatctat ctatctatct atctatctat ctatcgtct                 169

<210> SEQ ID NO 36
<211> LENGTH: 32
<212> TYPE: DNA

```
<213> ORGANISM: Homo sapiens

<400> SEQUENCE: 36
agaaagaaag aaagaaagaa agaaagaaag aa                                    32

<210> SEQ ID NO 37
<211> LENGTH: 14
<212> TYPE: DNA
<213> ORGANISM: Homo sapiens

<400> SEQUENCE: 37
tatctatcta tcta                                                        14

<210> SEQ ID NO 38
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: This sequence may encompass 8 to 27 'AGAA'
      repeating units

<400> SEQUENCE: 38
agaaagaaag aaagaaagaa agaaagaaag aaagaaagaa agaaagaaag aaagaaagaa      60
agaaagaaag aaagaaagaa agaaagaaag aaagaaagaa agaaagaa                  108

<210> SEQ ID NO 39
<211> LENGTH: 65
<212> TYPE: DNA
<213> ORGANISM: Homo sapiens

<400> SEQUENCE: 39
tctatctatc tgtctgtctg tctgtctatc tatctatcca tctatctatc tatccatcca     60
tccat                                                                  65
```

The invention claimed is:

1. An isolated single stranded nucleic acid consisting of a sequence selected from:

SEQ ID NO 1
TCTA TCTG TCTA (TCTG)$_4$ (TCTA)$_3$-;

SEQ ID NO 2
TCTA (TCTG)$_4$ (TCTA)$_7$-;

SEQ ID NO 3
(TCTA)$_2$ (TCTG)$_4$ (TCTA)$_3$, TCCA (TCTA)$_3$-;

SEQ ID NO 4
(TCAT)$_4$ CAT (TCAT)$_7$ TCGT TCAT-;

SEQ ID NO 7
(TTTC)$_3$ TTTT TTCT (CTTT)$_5$ T (CTTT)$_3$ CTCC (TTCC)$_2$-;

SEQ ID NO 8
(TTTC)$_3$ TTTT TTCT (CTTT)$_{13}$ CCTT (CTTT)$_5$ CTCC (TTCC)$_2$-;

SEQ ID NO 9
(TTTC)$_3$ TTTT TTCT (CTTT)$_{16}$ CCTT (CTTT)$_5$ CTCC (TTCC)$_2$-;

SEQ ID NO 10
(TTTC)$_4$ TTTT TT (CTTT)$_{15}$ (CTTC)$_3$ (CTTT)$_3$ CTCC (TTCC)$_4$-;

SEQ ID NO 11
(TTTC)$_4$ TTTT TT (CTTT)$_{16}$ (CTTC)$_3$ (CTTT)$_3$ CTCC (TTCC)$_4$-;

SEQ ID NO 12
(TTTC)$_4$ TTTT TT (CTTT)$_{17}$ (CTTC)$_3$ (CTTT)$_3$ CTCC (TTCC)$_4$-;

SEQ ID NO 13
(TTTC)$_4$ TTTT TT (CTTT)$_8$ (CTGT)$_4$ (CTTT)$_{13}$ (CTTC)$_4$ (CTTT)$_3$ CTCC (TTCC)$_4$-;

SEQ ID NO 14
(TTTC)$_4$ TTTT TT (CTTT)$_8$ (CTGT)$_5$ (CTTT)$_{13}$ (CTTC)$_4$ (CTTT)$_3$ CTCC (TTCC)$_4$-;

SEQ ID NO 15
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$-;

SEQ ID NO 16
(TTTC)$_4$ TTTT TT (CTTT)$_{10}$ (CTCT)$_5$ (CTTT)$_{13}$ (CTTC)$_4$ (CTTT)$_3$ CTCC (TTCC)$_4$-;

-continued

SEQ ID NO 17
(TTTC)$_4$ TTTT TT (CTTT)$_{12}$ (CTGT)$_5$
(CTTT)$_{14}$ (CTTC)$_3$ (CTTT)$_3$ CTCC (TTCC)$_4$-;

SEQ ID NO 18
(TTTC)$_2$ TTTT TT (CTTT)$_{14}$ (CTGT)$_3$
(CTTT)$_{14}$ (CTTC)$_4$ (CTTT)$_3$ CTCC (TTCC)$_4$-;

SEQ ID NO 19
(TCTA)$_4$ (TCTG)$_6$ (TCTA)$_3$ TA (TCTA)$_3$ TCA
(TCTA)2 TCCATA (TCTA)$_6$ TCGTCT-;

SEQ ID NO 20
(TCTA)$_5$ (TCTG)$_6$ (TCTA)$_3$ TCA (TCTA)$_2$
TCCATA (TCTA)$_9$ TCGTCT-;

SEQ ID NO 21
(TCTA)$_5$ (TCTG)$_6$ (TCTA)$_2$ TCA (TCTA)$_2$
TCCATA (TCTA)$_{10}$ TCGTCT-;

SEQ ID NO 22
(TCTA)$_4$ (TCTG)$_6$ (TCTA)$_3$ TA (TCTA)$_3$
TCA (TCTA)$_2$ TCCATA (TCTA)$_8$ TCGTCT-;

SEQ ID NO 23
(TCTA)$_5$ (TCTG)$_5$ (TCTA)$_3$ TA (TCTA)$_3$
TCA (TCTA)$_2$ TCCATA (TCTA)$_9$ TCGTCT-;

SEQ ID NO 24
(TCTA)$_4$ (TCTG)$_6$ (TCTA)$_3$ TA (TCTA)$_3$
TCA (TCTA)$_2$ TCCATA (TCTA)$_{10}$ TCGTCT-;

SEQ ID NO 25
(TCTA)$_4$ (TCTG)$_6$ (TCTA)$_3$ TA (TCTA)$_3$ TCA
(TCTA)$_2$ TCCATA (TCTA)$_{11}$ TCGTCT-;

SEQ ID NO 26
(TCTA)$_6$ (TCTG)$_5$ (TCTA)$_3$ TA (TCTA)$_3$
TCA (TCTA)$_2$ TCCATA (TCTA)$_{11}$ TCGTCT-;

SEQ ID NO 27
(TCTA)$_5$ (TCTG)$_6$ (TCTA)$_3$ TA (TCTA)$_3$
TCA (TCTA)$_2$ TCCATA (TCTA)$_{12}$ TCGTCT-;

SEQ ID NO 28
(TCTA)$_5$ (TCTG)$_6$ (TCTA)$_3$ TA (TCTA)$_3$ TCA
(TCTA)$_2$ TCCATA (TCTA)$_{11}$ TA TCTA TCGTCT-;

SEQ ID NO 29
(TCTA)$_5$ (TCTG)$_6$ (TCTA)$_3$ TA (TCTA)$_3$ TCA
(TCTA)$_2$ TCCATA (TCTA)$_{12}$ TA TCTA TCGTCT-;

SEQ ID NO 30
(TCTA)$_5$ (TCTG)$_6$ (TCTA)$_3$ TA (TCTA)$_3$ TCA
(TCTA)$_2$ TCCATA (TCTA)$_{13}$ TA TCTA TCGTCT-;

SEQ ID NO 31
(TCTA)$_5$ (TCTG)$_6$ (TCTA)$_3$ TA (TCTA)$_3$ TCA
(TCTA)$_2$ TCCATA (TCTA)$_{14}$ TATCTA TCGTCT-;

SEQ ID NO 32
(TCTA)$_{10}$ (TCTG)$_5$ (TCTA)$_3$ TA (TCTA)$_3$ TCA
(TCTA)$_2$ TCCATA (TCTA)$_{12}$ TCGTCT-;

SEQ ID NO 33
(TCTA)$_{11}$ (TCTGT)$_5$ (TCTA)$_3$ TA (TCTA)$_3$ TCA
(TCTA)$_2$ TCCATA (TCTA)$_{12}$ TCGTCT-;

SEQ ID NO 34
(TCTA)$_{11}$ (TCTG)$_5$ (TCTA)$_3$ TA (TCTA)$_3$ TCA
(TCTA)$_2$ TCCATA (TCTA)$_{13}$ TCGTCT;

SEQ ID NO 35
(TCTA)$_{13}$ (TCTG)$_5$ (TCTA)$_3$ TA (TCTA)$_3$
TCA (TCTA)$_2$ TCCATA (TCTA)$_{12}$ TCGTCT;
and

SEQ. ID NO: 36
(AGAA)$_8$-.

wherein the isolated single-stranded nucleic acid is covalently labeled with a dye.

* * * * *